United States Patent
Lehrer et al.

[11] Patent Number: 5,998,374
[45] Date of Patent: Dec. 7, 1999

[54] CLAVASPIRINS

[75] Inventors: Robert I. Lehrer, Santa Monica, Calif.; In-Hee Lee, Seoul, Rep. of Korea; Chengquan Zhao, Los Angeles, Calif.

[73] Assignee: The Regents of University of California, Oakland, Calif.

[21] Appl. No.: 08/808,277

[22] Filed: Feb. 28, 1997

[51] Int. Cl.$^6$ .......................... C07K 14/435; A61K 38/17
[52] U.S. Cl. .......................... 514/13; 530/323; 530/326; 530/332
[58] Field of Search ................. 514/13; 530/323, 530/326, 332

[56] References Cited

PUBLICATIONS

Bensch, K.W. et al. *FEBS Lett* (1995) 368:331.
Christensen, B. et al. *Proc Natl Acad Sci USA* (1988) 85:5072.
Cornelissen, B.J.C. et al. *Plant Physiol* (1993) 101:709–712.
Diamond, G. et al. *Proc Natl Acad Sci USA* (1991) 88:3952.
Duclohier, H. et al. *Biophys J* (1989) 56:1017.
Harwig, S.S.L. et al. *FEBS Lett* (1994) 342:281.
Jones, D.E. et al. *J. Biol Chem* (1992) 267:23216.
Kokryakov, V.N. et al. *FEBS Lett* (1993) 231.
Lehrer, R.I. et al. *Ann Rev Immunol* (1992) 11:105.
Nakamura, T. et al., *J Biol Chem* (1988) 263:16709–16713.
Patterson–Delafield, J. et al. *Infect Immun* (1980) 30:180.
Schonwetter, B.S. et al. *Science* (1995) 267:1645.
Selsted, M.E. et al. *J. Biol Chem* (1993) 268:6641.
Terry, A.S. et al. *J Biol Chem* (1988) 263:5745.
Zasloff, M. *Proc Natl Acad Sci USA* (1987) 84:5449.
Zasloff, M. *Proc Natl Acad Sci USA* (1988) 85:910.
I.H. Lee et al., "Clavanins, Alpha–Helical Antimicrobial Peptides From Tunicate Hemocytes", FEBS Letts. 400(2): 158–162, Jan. 1997.

*Primary Examiner*—Rebecca E. Prouty
*Attorney, Agent, or Firm*—Morrison & Foerster LLP

[57] ABSTRACT

Novel microbial peptides called clavaspirins are of the formula (SEQ ID NO:1)

$$X'_1 X_2 B'_3 X_4 X_5 U_6 U_7 X_8 X_9 B_{10} X'_{11} X_{12} U_{13} B_{14} X_{15} X_{16} B^*_{17} B_{18} X_{19} U_{20} X_{21} X'_{22} X_{23} \quad (1)$$

including the salts, esters, amides and acylated forms thereof wherein X is a hydrophobic amino acid residue or modified form thereof;

X' is a small or a hydrophobic amino acid residue or a modified form thereof;

B is a basic amino acid residue or modified form thereof;

B' is basic or a polar/large amino acid residue or modified form thereof;

B* is a basic or a hydrophobic amino acid residue or a modified form thereof; and U is a small amino acid residue or modified form thereof.

12 Claims, 15 Drawing Sheets

```
  1  GACAAACAACAGGAAAGATGAAACAACAATTTGATTCTTCTCATACTGGGACTTGGCA
                    M  K  T  T  I  L  L  I  L  I  L  G  L  G

61  TCAATGCAAAATCTCTGGAGGAAGAAAATCGGAGGAAGAGAAAGTATTCCAATTCCTTG
      I  N  A  K  S  L  E  E  R  K  S  E  E  E  K  V  F  Q  F  L

121  GCAAAATTATTCATCATGTTGGCAATTTTGTACATGGTTTTAGCCACGTGTTCGGCGACG
      G  K  I  I  H  H  V  G  N  F  V  H  G  F  S  H  V  F  G  D

181  ACCAACAAGATAATGGAAAGTTTTATGGCCACTACGCAGAAGACAATGGCAAGCATTGGT
      D  Q  Q  D  N  G  K  F  Y  G  H  Y  A  E  D  N  G  K  H  W

241  ATGATACCGGGGATCAATAAAAAAGTTTTAAACAGCTACGCGACTTGAAGACGGACGGAC
      Y  D  T  G  D  D  Q  ***

301  CCGGCAGAACATTGATATTTCTTGTTTCTTTGATTAAAGGCTAGCCTTATTACTCAGAA

361  TATAACACTACATTGCATTC(A)n
```

FIG. 1A

```
  1 CAAACTCAGAGACAAACAACAGGAAACAATGAAAACAATTTTGATTCTTCTCATACTGGG
                          M  K  T  T  I  L  I  L  L  I  L  G

61 ACTTGGCATCAATGCAAAATCTCTGGAGGAAGAAATCGGAGGAAGAAAAAGTATTCCA
     L  G  I  N  A  K  S  L  E  E  R  K  S  E  E  E  K  V  F  H

121 TCTCCCTTGGCAAAATTATTCATCATGTTGGCAATTTTGTATATGGTTTTAGCCACGTGTT
     L  L  G  K  I  I  H  H  V  G  N  F  V  Y  G  F  S  H  V  F

181 CGGCGACGACCAACAAGATAATGGGAAATGGAAAGTTTTATGGCCACTACGCAGAAGACAATGGCAA
     G  D  D  Q  Q  D  N  G  K  F  Y  G  H  Y  A  E  D  N  G  K

241 GCATTGGTATGATACCGGGGATCAATAAAAAAGTTTTAAACAGCTACGCGACTTGAAGAC
     H  W  Y  D  T  G  D  D  Q  *  *  *

301 GGACGGACCCGGGCAGAACATTGATATTTCTTGTTTCTTTGATTAAAGGCTAGCCTTATT

361 ACTCAGAATATAACACTACATTGCATTC(A)n
```

FIG. 1B

```
1    CAAACTCAGACAAACAACAGGAAAGATGAAAACAACAATTTTGATTCTTCTCATACTGGG
                                  M  K  T  T  I  L  L  I  L  L  G

61   ACTTGGCATCAATGCAAATCTCTGGAGGAAAGAAATCGGAGGAAGAGAAAGCTTTCAA
     L  G  I  N  A  K  S  L  E  E  R  K  S  E  E  E  K  A  F  K

121  ACTCCCTTGGCAGAATTATTCATCATGTTGGCAATTTTGTATATGGTTTTAGCCACGTGTT
     L  L  G  R  I  I  H  H  V  G  N  F  V  Y  G  F  S  H  V  F

181  CGGCGACGACCAACAGATAATGGAAAGTTTTATGGCCACTACGCAGAAGACAATGGCAA
     G  D  D  Q  Q  D  N  G  K  F  Y  G  H  Y  A  E  D  N  G  K

241  GCATTGGTATGATACCGGGGATCAATAAAAAGTTTTAAACAGCTACGCCGACTTGAAGAC
     H  W  Y  D  T  G  D  D  Q  *  *  *

301  GGACGGACCCGGCAGAACATTGATATTTCTTGTTTTCTTTGATTAAAGGCTAGCCCTTATT

361  ACTCAGAATATAACACTACATTGCATTC(A)n
```

FIG. 1C

```
  1  CAAACTCAGACAAACAACAGGAAAGATGAAAACAATTTTGATTCTTCTCATACTGGG
                           M  K  T  T  I  L  I  L  L  I  L  G

61  ACTTGGCATCAATGCAAATCTCTGGAGGAAGAGAAATTATTCAA
      L  G  I  N  A  K  S  L  E  E  R  K  S  E  E  E  K  L  F  K

121  ACTCCTTGGCAAATTATTCATCATGTTGGCAATTTTGTACATGGTTTTAGCCACGTGTT
      L  L  G  K  I  H  H  H  V  G  N  F  V  H  G  F  S  H  V  F

181  CGGCGACGACCAACAAGATAATGGAAAGTTTTATGGCTACTACGCAGAAGACAATGGCAA
      G  D  D  Q  Q  D  N  G  K  F  Y  G  Y  Y  A  E  D  N  G  K

241  GCATTGGTATGATACCGGGGATCAATAAAAAAGTTTAAACAGCTACGCGACTTGAAGAC
      H  W  Y  D  T  G  D  Q  *  *  *

301  GGACGGACCCGGCAGAACATTGATATTTCTGTTTTCTTTGATTAAAGGCTAGCCCTTATT

361  ACTCAGAATATAACACTACATTGCATTC(A)n
```

FIG. 1D

```
ATC AAA CTC AGA CAA ACA ACA GGA AAG ATG AAA ACA ATA ATT TTG  45
                                 M   K   T   I   I   L    6

ATT CTA CTC ATA TTG GGA CTT GGC ATC GAT GCA AAA TCC CTG GAG  90
 I   L   L   I   L   G   L   G   I   D   A   K   S   L   E   21

GAA AGC AAA GCG GAC GAA GAG AAA TTC CTC CGT TTC ATT GGC AGC 135
 E   S   K   A   D   E   E   K   F   L   R   F   I   G   S   36

GTT ATA CAT GGT ATT GGA CAA CAA CAC CTT GTA CAT CAT ATT GGC GCA 180
 V   I   H   G   I   G   Q   Q   H   L   V   H   H   I   G   A   51

GTT ATA CAT GGT ATT GGA CAA CAA CAC CTT GTA CAT CAT ATT GGC GCA 180
 V   I   H   G   I   G   Q   Q   H   L   V   H   H   I   G   A   51

TTA GGC GAC GAC GAC CAA GAT AAT GGA AAG TTT TAT GGC TAC TAC 225
 L   G   D   D   D   Q   D   N   G   K   F   Y   G   Y   Y   66

GCA GAA GAC AAT GGC AAG CAT TGG TAT GAT ACC GGG GAT CAA TAA 270
 A   E   D   N   G   K   H   W   Y   D   T   G   D   Q   *    80

AAA AGT TTT AAA TTG ATA TTT CTT GTT TTC TTT GAT TAA AGG CTA GCC 315

AGA ACA TTG ATA TAA CAC TAC ATT GCA TTC (A)n                   360

TTA CTC AGA ATA TAA                                             390
```

FIG. 1E

SIGNAL SEQUENCE AND ANIONIC PROPIECE

```
CLAV_A    MKTTILILILGLGINAKSLEERKSEEEK
          ||||||||||||||||||||||||||||
CLAV_C    MKTTILILILGLGINAKSLEERKSEEEK
          ||||||||||||||||||||||||||||
CLAV_D    MKTTILILILGLGINAKSLEERKSEEEK
          ||||||||||||||||||||||||||||
CLAV_E    MKTTILILILGLGINAKSLEERKSEEEK
```

MATURE PEPTIDE AND ANIONIC POSTPIECE

```
CLAV_A    VFQFLGKIIHHVGNFVHGFSHVFGDDQQDNGKFYGHYAEDNGKHWYDTGDQ
          |..|||||||||||||||||||||||||||||||||||||||||||||||
CLAV_C    VFHLLGKIIHHVGNFVYGFSHVFGDDQQDNGKFYGHYAEDNGKHWYDTGDQ
          |.|.|||||||||||||||||||||||||||||||||||||||||||||||
CLAV_D    AFKLLGRIIHHVGNFVYGFSHVFGDDQQDNGKFYGHYAEDNGKHWYDTGDQ
          .|.||||||||||||||||||||||||||||||||||||||||||||||||
CLAV_E    LFKLLGKIIHHVGNFVHGFSHVFGDDQQDNGKFYGYYAEDNGKHWYDTGDQ
```

FIG. 1F

```
lavaspirin-1    C----TCAGACAAACAACAGGAAAGATGAAAACAATAATTTTGATTCTAC  -46
                |    ||||||||||||||||||||||||||||| ||||||||||||| |
CLAVC         - CAAACTCAGACAAACAACAGGAAAGATGAAAACAACAATTTTGATTCTTC  -50 lavaspirin-1  - TCATATTGGGACTTGGCATCGATGCAAAATCCCTGGAGGAAAGCAAAGCG  -96
                ||||| ||||||||||||||| |||||||| |||||||||||||| || ||
CLAVC         - TCATACTGGGACTTGGCATCAATGCAAAATCTCTGGAGGAAAGAAAATCG  -100 lavaspirin-1  - GACGAAGAGAAA---TTCC-TCCGTTTCATTGGCAGCGTTAT--A-CATG  -139
                || ||||| |||   |||| ||  || ||||||  ||||    |  ||||
CLAVC         - GAGGAAGAAAAAGTATTCCATC----TCCTTGGCAAAATTATTCATCATG  -146 lavaspirin-1  - GTATTGGACACCTT-GTACATCATATTGGC---GTCGCATTAGGCGACGA  -185
                ||||  ||  || ||   | |||  || | |  || ||||||||
CLAVC         - ---TTGG-CAATTTTGTATATGGTTTTAGCCACGT-G--TTCGGCGACGA  -189 lavaspirin-1  - CCAACAAGATAATGGAAAGTTTTATGGCTACTACGCAGAAGACAATGGCA  -235
                |||||||||||||||||||||||||||| |||||||||||||||||||||
CLAVC         - CCAACAAGATAATGGAAAGTTTTATGGCCACTACGCAGAAGACAATGGCA  -239 lavaspirin-1  - AGCATTGGTATGATACCGGGGATCAATAAAAAAGTTTTAAACAGCTACGC  -285
                ||||||||||||||||||||||||||||||||||||||||||||||||||
CLAVC         - AGCATTGGTATGATACCGGGGATCAATAAAAAAGTTTTAAACAGCTACGC  -289 lavaspirin-1  - GACTTGAAGACGGACGGACCCGGCAGAACATTGATATTTCTTGTTTTCTT  -335
                ||||||||||||||||||||||||||||||||||||||||||||||||||
CLAVC         - GACTTGAAGACGGACGGACCCGGCAGAACATTGATATTTCTTGTTTTCTT  -339 lavaspirin-1  - TGATTAAAGGCTAGCCTTATTACTCAGAATATAACACTACATTGCATTC  -384
                |||||||||||||||||||||||||||||||||||||||||||||||||
CLAVC         - TGATTAAAGGCTAGCCTTATTACTCAGAATATAACACTACATTGCATTC  -388
```

FIG. 2

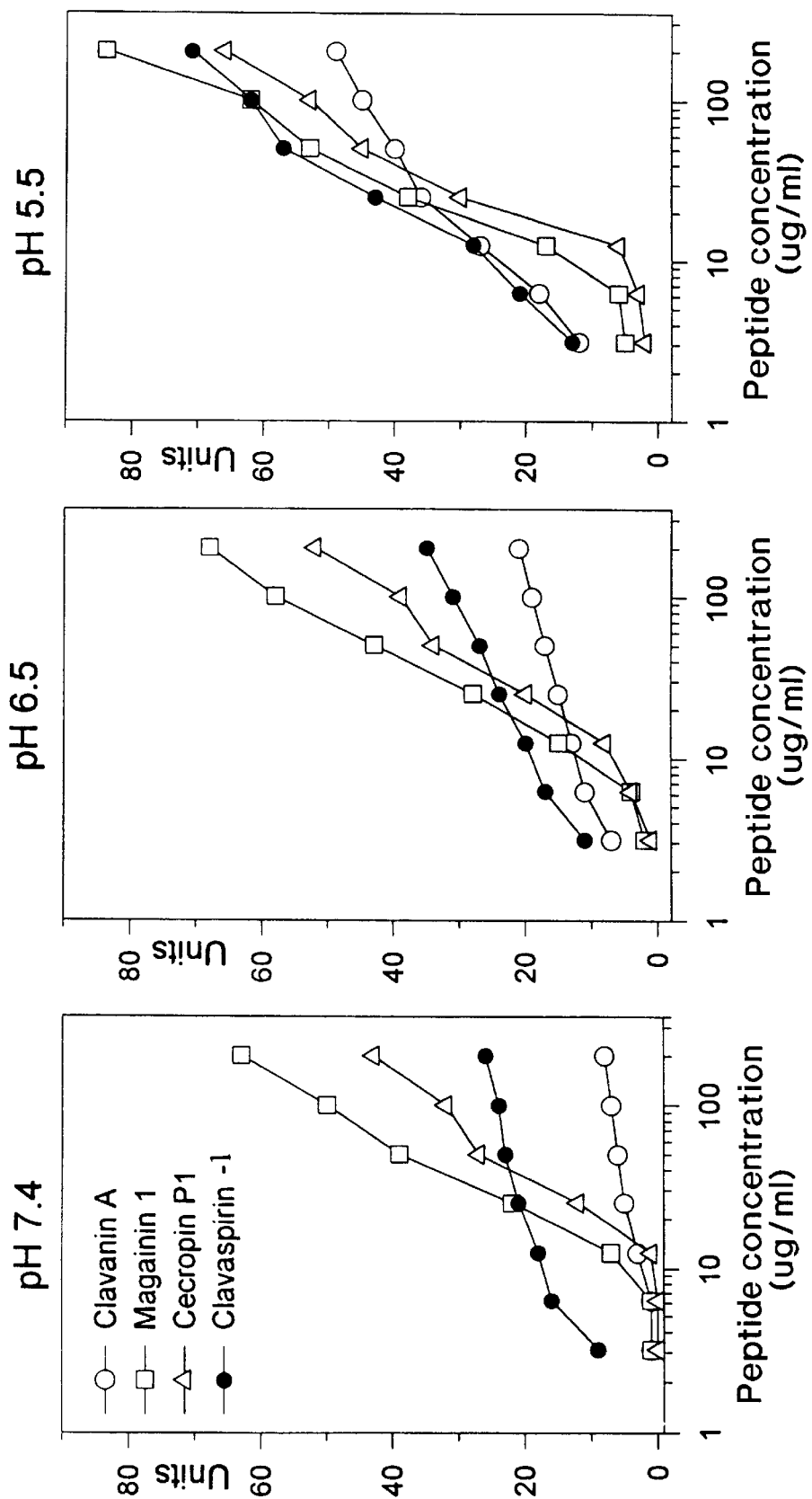

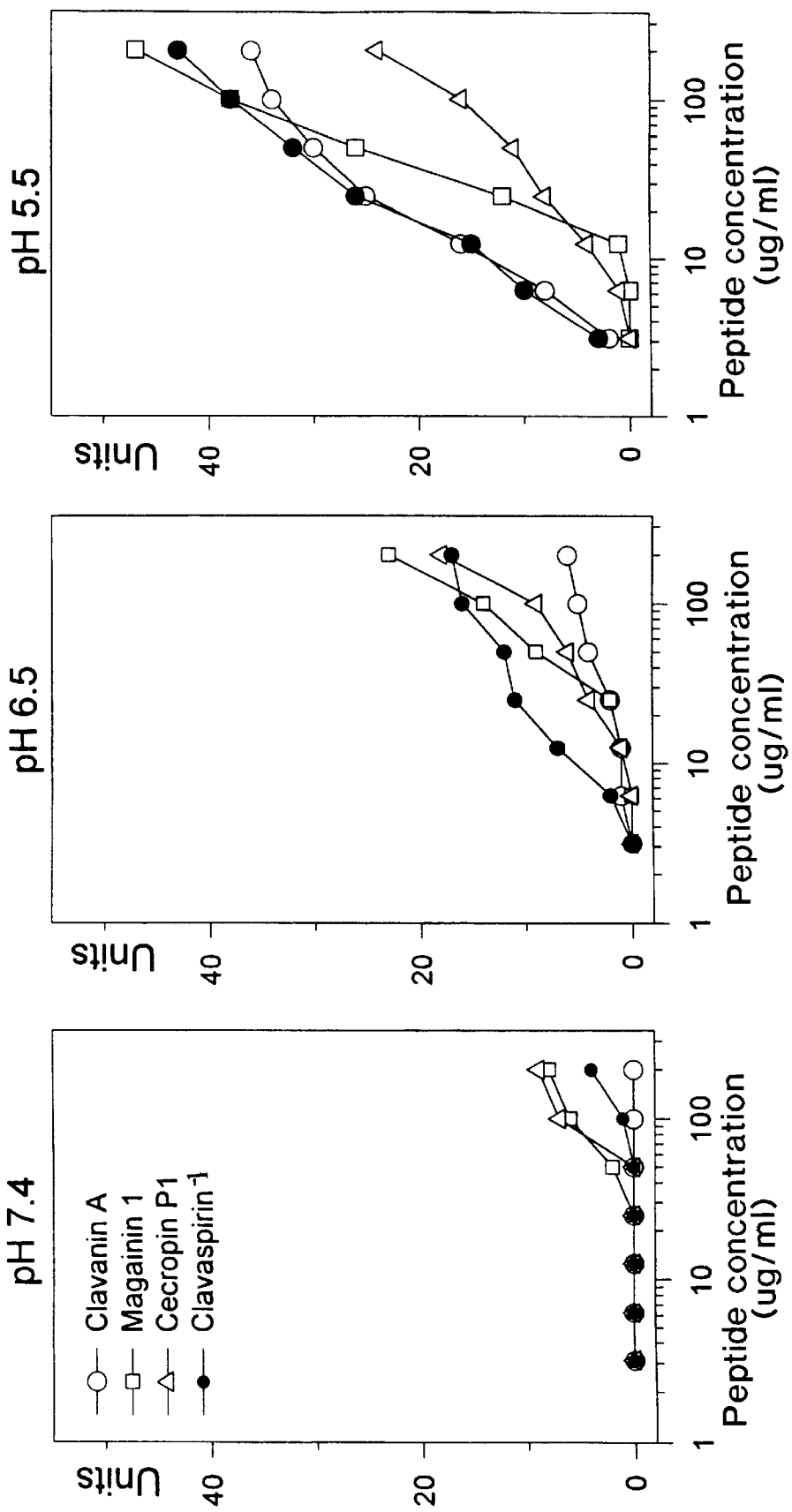

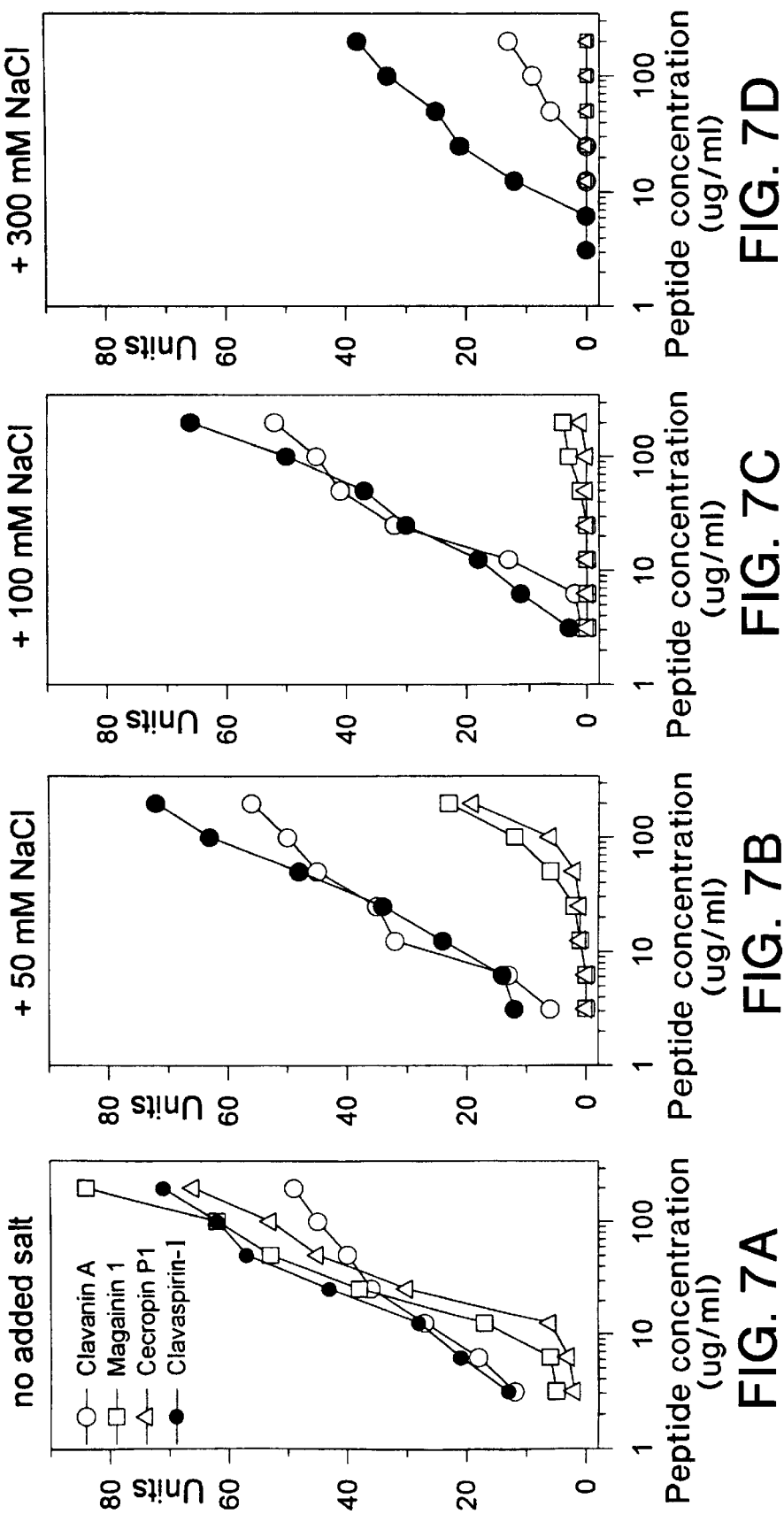

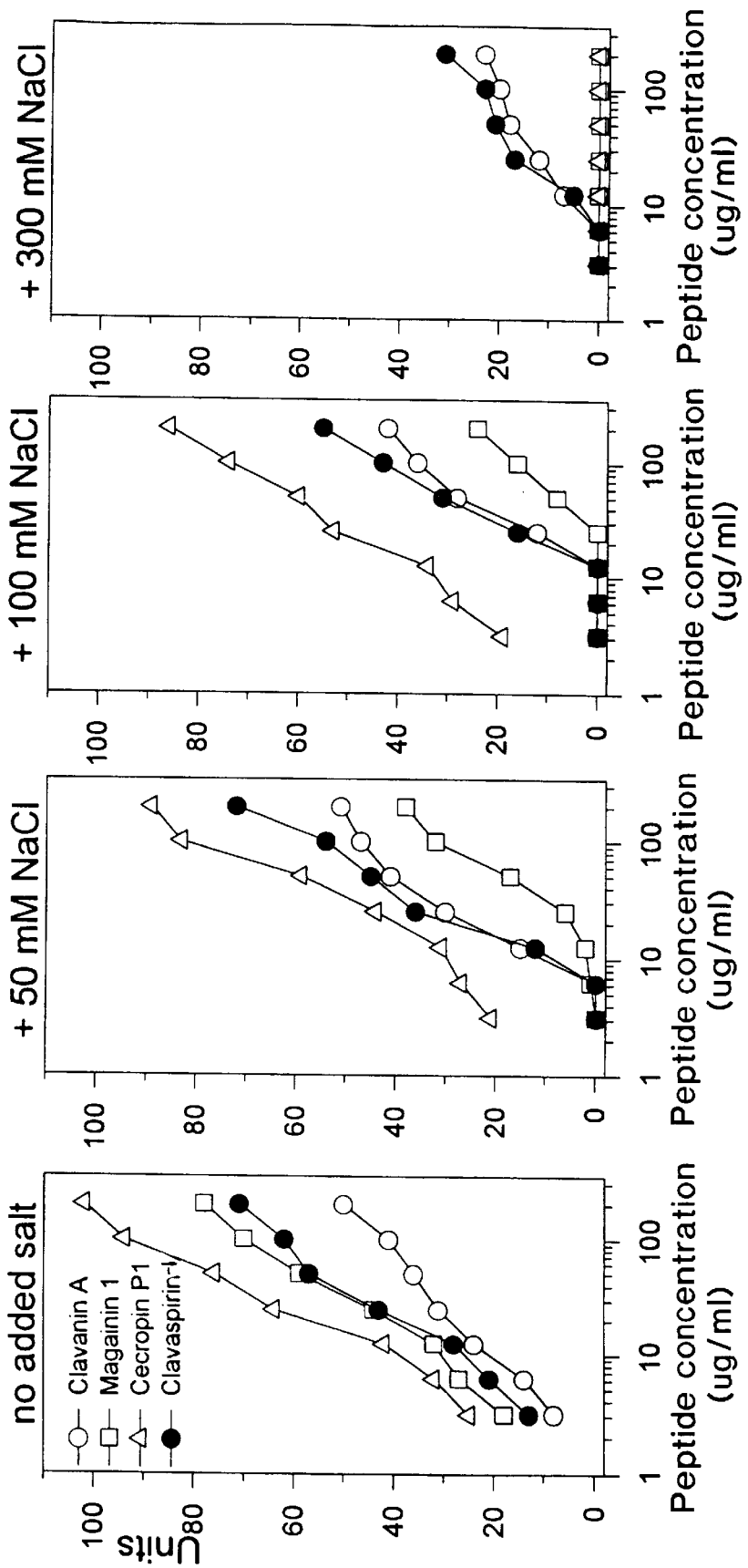

CLAVASPIRINS

ACKNOWLEDGMENT OF GOVERNMENT SUPPORT

This invention was made at least in part with funding from NIH grant numbers 1-PO1-AI-37945-01 and 5R37-AI-22839-10. The U.S. Government has certain rights in this invention.

TECHNICAL FIELD

The invention relates to a class of peptide and peptide-like compounds with antimicrobial activity. These peptides, designated "clavaspirins" are characterized by patterns of basic and hydrophobic amino acids which result in compounds with a spectrum of antimicrobial activities.

BACKGROUND ART

Antimicrobial peptides have been isolated from a wide variety of animal sources. These sources include, prominently, leukocytes of humans (Lehrer, R. I. et al., *Ann Rev Immunol* (1992) 11:105); pigs (Kokryakov, V. N. et al., *FEBS Lett* (1993) 231); bovine sources (Selsted, M. E. et al., *J Biol Chem* (1993) 268:6641); rabbits (Patterson-Delafield, J. et al., *Infect Immun* (1980) 30:180); and birds (Harwig, S. S. L. et al., *FEBS Lett* (1994) 342:281). Antimicrobial peptides have also been found in bovine tongue (Schonwetter, B. S. et al., *Science* (1995) 267:1645) respiratory tract epithelia (Diamond, G. et al., *Proc Natl Acad Sci USA* (1991) 88:3952) and gastrointestinal and genital urinary tracts of humans and animals (Jones, D. E. et al., *J Biol Chem* (1992) 267:23216; Bensch, K. W. et: al., *FEBS Lett* (1995) 368:331). In addition, antimicrobial peptides have been isolated from the hemocytes of the Horseshoe Crab as described by Nakamura, T. et al., *J Biol Chem* (1988) 263:16709–16713. These various antimicrobial peptides, for example the tachyplesins, polyphemusins, defensins, clavanins and gallinacins, are typically characterized by specific positions of cysteine residues which putatively control conformation of the molecule.

An additional class of antimicrobial peptides, found in the skin of the African clawed frog, *Xenopus laevis*, are α-helical (noncovalent-cyclic) peptides (Zasloff, M., *Proc Natl Acad Sci USA* (1987) 84:5449). This class of antimicrobial peptides, called the magainins, in their mature form contain, 23 amino acids and are α-helical but not amidated. The magainins possess broad spectrum antimicrobial activity (Harwig, S. S. L. et al., *FEBS Lett* (1994) 342:281; Zasloff, M. et al., *Proc Natl Acad Sci USA* (1988) 85:910). The nature of the antimicrobial activity as related to the α-helical amphipathic structure of magainins has been studied (Duclohier, H. et al., *Biophys J* (1989) 56:1017) as has that of another class of α-helical antimicrobial peptides, the cecropins (Christensen, B. et al., *Proc Natl Acad Sci USA* (1988) 85:5072. The magainins are synthesized from a large prepropeptide containing a single copy of Magainin-1 and five copies of the closely related Magainin-2 (Terry, A. S. et al., *J Biol Chem* (1988) 263:5745).

Antimicrobial peptides and proteins have also been found in plants as reviewed by Cornelissen, B. J. C. et al., *Plant Physiol* (1993) 101:709–712.

The present invention is directed to a class of peptides and peptide-like compounds several members of which may be isolated from the hemocytes of the tunicate Styela clava. Tunicates are simple marine invertebrates whose larval forms contain a constellation of features establishing their kinship to early vertebrates. The body cavity of the mature tunicate provides an acceptable source of mesoderm-derived phagocytes (hemocytes) that are counterparts to the blood leukocytes of higher vertebrates. It is known that phagocytes of freshly harvested colonial tunicates are often filled with various bacteria and that the introduction of bacteria beneath the tunic is capable of inducing phagocytic cells to traverse the underlying epithelium and surround these foreign objects.

Co-pending Application Attorney Docket number 22000–20563.00 filed Nov. 6, 1996 describes a class of peptides isolated from *Styela clava* which are designated the clavanins. These peptides have a distinctive pattern of basic and hydrophobic amino acids side-chains. The present invention relates to another class of peptides also obtainable from these organisms which have a different pattern of amino acid sequence but also are antimicrobial. These peptides are therefore designated "clavaspirins."

DISCLOSURE OF THE INVENTION

The invention is directed to a class of peptides and peptide-like compounds, the clavaspirins, that are characterized by specific patterns of basic and hydrophobic amino acid side-chains and which show a broad spectrum of antimicrobial activity. The clavaspirins are therefore useful additions to the repertoire of agents useful in preserving materials otherwise susceptible to microbial degradation, in protecting plants against bacterial infection, and in therapeutic and prophylactic protection of animals against bacteria, fungi and viruses. As used in the present application "antimicrobial" refers to the ability to inhibit the growth of, destroy, or otherwise impede the undesired destructive effects of such replicable forms.

Thus, in one aspect, the invention is directed to compounds of the formula (SEQ ID NO:1):

$$X'_1 X_2 B'_3 X_4 X_5 U_6 U_7 X_8 X_9 B_{10} X'_{11} X_{12} U_{13} B_{14} X_{15} X_{16} B^*_{17} B_{18} X_{19} U_{20} X_{21} X'_{22} X_{23} \quad (1)$$

including the salts, esters, amides and acylated forms thereof wherein X is a hydrophobic amino acid residue or modified form thereof;

X' is a small or a hydrophobic amino acid residue or a modified form thereof;

B is a basic amino acid residue or modified form thereof;

B' is basic or a polar/large amino acid residue or modified form thereof;

B* is a basic or a hydrophobic amino acid residue or a modified form thereof; and U is a small amino acid residue or modified form thereof.

In other aspects, the invention is directed to recombinant materials useful for the production of those peptides of the invention that contain gene-encoded amino acids, as well as plants or animals modified to contain expression systems for the production of these peptides. The invention also includes methods to prepare and manipulate these recombinant materials.

In addition, the invention is directed to pharmaceutical compositions and compositions for application to plants and to materials whose preservation from microbial growth is desired, which compositions contain the compounds of the invention as active ingredients and to compositions which contain expression systems for the production of the peptides for in situ expression of the nucleotide sequence encoding these peptides. The invention is also directed to methods to prepare the invention compounds synthetically, to antibodies specific for these compounds, and to the use of the compounds as preservatives, therapeutics, and prophylactics. The invention is also directed to the use of the compounds of the invention as standards in antimicrobial assays and as affinity ligands for adsorption of counterpart structures in microbes, including viruses, as set forth above.

BRIEF DESCRIPTION OF THE DRAWINGS

FIGS. 1A (SEQ ID NO:2 and 3), 1B (SEQ ID NO:4 and 5), 1C (SEQ ID NO:6 and 7), 1D (SEQ ID NO:8 and 9), 1E (SEQ ID NO:10 and 11), 1F (SEQ ID NO:3,5,7 and 9) show the sequences of cDNA encoding clavaspirin-1 and those for cDNA encoding the clavanins.

FIG. 2 (SEQ ID NO:10 and 4) shows a comparison of the nucleotide sequence encoding Clavanin C and clavaspirin-1.

FIGS. 4A–4C show the antimicrobial activity of clavaspirin-1 against *Listeria monocytogenes* at various pHs.

FIGS. 6A–6C show the antimicrobial activity of clavaspirin-1 against *Candida albicans* at various pHs.

FIGS. 7A–7D show the antimicrobial activity of clavaspirin-1 against *L. monocytogenes* at various salt concentrations.

FIGS. 8A–8D show the antimicrobial activity of clavaspirin-1 against *E. coli* at various salt concentrations.

MODES OF CARRYING OUT THE INVENTION

Figure 3:
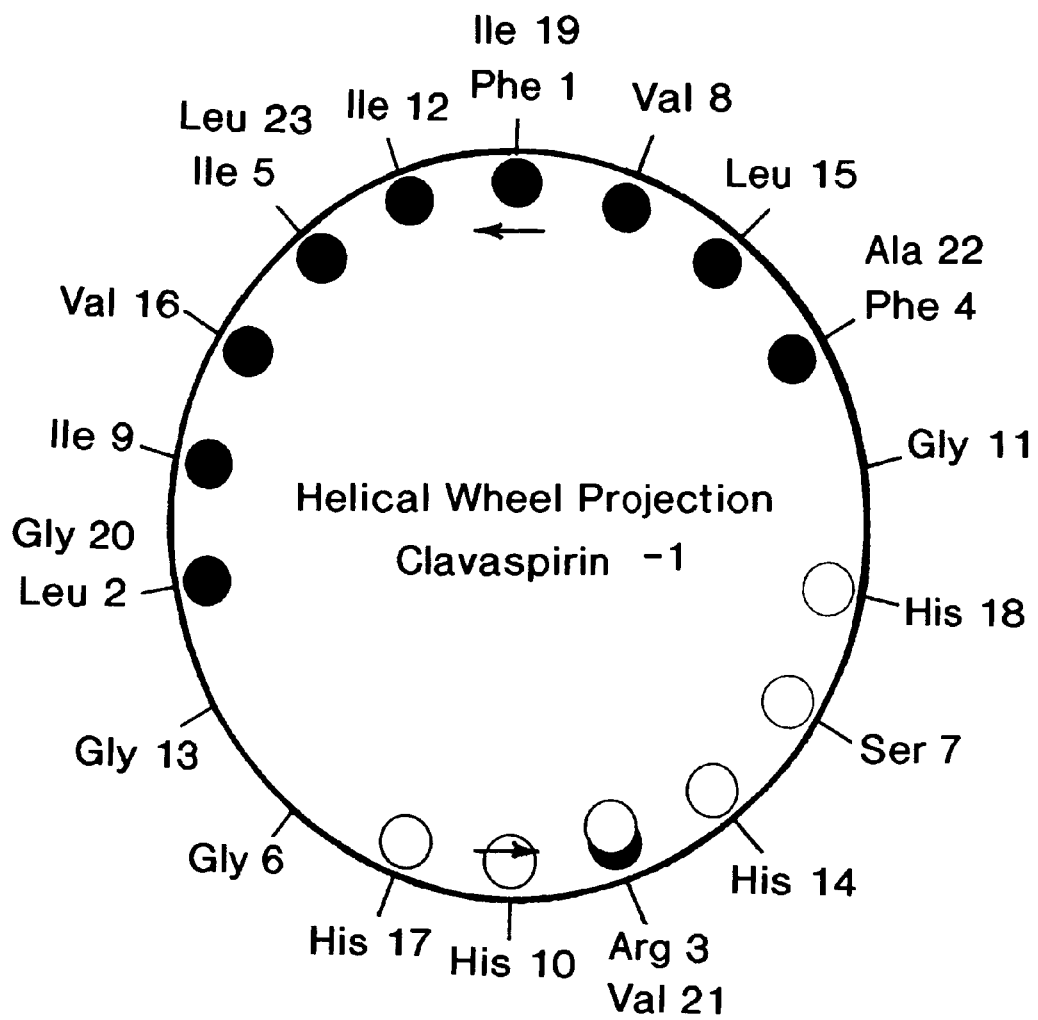
FIG. 3 shows a helical wheel projection of clavaspirin-1 showing its amphipathicity.

The compounds of the invention are generally described by the formula (SEQ ID NO:1)

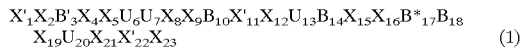

$$X'_1 X_2 B'_3 X_4 X_5 U_6 U_7 X_8 X_9 B_{10} X'_{11} X_{12} U_{13} B_{14} X_{15} X_{16} B^*_{17} B_{18} X_{19} U_{20} X_{21} X'_{22} X_{23} \quad (1)$$

and the salts, esters, amides, and acyl forms thereof. Each position represented by a letter indicates a single amino acid residue although, as described below, one or more of the peptide linkages between such residues may be replaced by a peptide linkage mimic. The invention compounds include those represented by formula (1) as well as analogous peptides which are isolable from the hemocytes of tunicates. "Analogous" forms are those which retain the ability to form an α-helical configuration, are antimicrobial, and are linear (rather than disulfide) in configuration/conformation.

The amino terminus of the peptide may be in the free amino form or may be acylated by a group of the formula RCO—, wherein R represents a hydrocarbyl group of 1–6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The amino acids in the peptides of the invention may be those encoded by the gene or analogs thereof, and may also be the D-isomers thereof. One preferred embodiment of the peptides of the invention is that form wherein all of the residues are in the D-configuration thus conferring resistance to protease activity while retaining antimicrobial or antiviral properties. The resulting clavaspirins are themselves enantiomers of the native L-amino acid-containing forms.

The amino acid notations used herein are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer at the α carbon is intended unless the D-form is expressly indicated by a dagger superscript (†).

The compounds of the invention are peptides or peptide-like compounds which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at the relevant pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

| | |
|---|---|
| Acidic | Aspartic acid and Glutamic acid |
| Basic | Noncyclic: Arginine, Lysine |
| | Cyclic: Histidine |
| Small | Glycine, Serine, Alanine, Threonine |
| Polar/large | Asparagine, Glutamine |
| Hydrophobic | Tyrosine, Valine, Isoleucine, Leucine, Methionine, Phenylalanine, Tryptophan |

The gene-encoded secondary amino acid proline is a special case due to its known effects on the secondary conformation of peptide chains, and is not, therefore, included in a group. Cysteine residues are also not included in these classifications since their capacity to form disulfide bonds to provide secondary structure may override the general polarity/nonpolarity of the residue. However, if a cysteine, which is, technically speaking, a small amino acid, is modified so as to prevent its participation in secondary structure, those locations indicated "S" in the compound of formula (1) may be inhabited by such modified cysteine residues. In addition, a single cysteine residue may occupy a position indicated by "S" although this is less favored because of the possibility of formation of intermolecular disulfides which may denature the antimicrobial activity of the compounds.

The "modified" amino acids that may be included in the clavaspirins are gene-encoded amino acids which have been processed after translation of the gene, e.g., by the addition of methyl groups or derivatization through covalent linkage to other substituents or oxidation or reduction or other covalent modification. The classification into which the resulting modified amino acid falls will be determined by the characteristics of the modified form. For example, if lysine were modified by acylating the $\epsilon$-amino group, the modified form would not be classed as basic but as polar/large.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); $\beta$-2-thienylalanine (Thi); methionine sulfoxide (MSO); and homoarginirie (Har). These also fall conveniently into particular categories.

Based on the above definitions,

Sar, beta-Ala and Aib are small;

t-BuA, t-BuG, N-MeIle, Nle, Mvl, Cha, Phg, Nal, Thi and Tic are hydrophobic;

2,3-diaP, Orn and Har are basic;

Cit, Acetyl Lys and MSO are neutral/polar/large.

The various omega-amino acids are classified according to size as small (beta-Ala and 3-aminopropionic) or as large and hydrophobic (all others).

Other amino acid substitutions for those encoded in the gene can also be included in peptide compounds within the scope of the invention and can be classified within this general scheme according to their structure.

In all of the "peptides" of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M. M., *J Chem Soc Perkin Trans I* (1982) 307–314 (—CH═CH—, cis and trans); Almiquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—C(OH) CH$_2$—); and Hruby, V. J., *Life Sci* (1982) 31:189–199 (—CH$_2$—S—).

The compounds of formula (1) are generally defined as set forth in the Disclosure of the Invention set forth above.

Preferred embodiments include those wherein

X'$_1$ is Phe, Trp, Tyr, or Ala; or

X$_2$ is Val, Leu, Ile, Phe, Trp or Tyr; or

B'$_3$ is Asn, Gln, His, Lys or Arg; or

X$_4$ and X$_5$ is each independently selected from the group consisting of Phe, Leu, Tyr, Ile and Val; or U$_6$ is Gly, Ser or Ala, preferably Gly; or $U_7$ Gly, Ser or Ala; or $X_8$ and $X_9$ is each independently selected from the group consisting of Ile, Leu and Val; or $B_{10}$ is His, Lys or Arg, preferably His; or $X'_{11}$ is Ala, Ser or Gly; or $X_{12}$ is Val, Ile or Leu; or $U_{13}$ is Ala, Ser or Gly, preferably Gly; or $B_{14}$ is Arg, Lys or His, preferably His; or $X_{15}$ and $X_{16}$ is each independently selected from the group consisting of Val, Leu and Ile, preferably $X_{15}$ is Val, Ile or Leu and $X_{16}$ is Val; or $B^*_{17}$ is His, Lys, Arg, Trp, Phe or Tyr or a modified form thereof, preferably His; or $B_{18}$ is Arg, Lys or His, preferably His; or $X_{19}$ is Leu, Ile or Val, preferably Ile; or $U_{20}$ is Gly, Ala or Ser, preferably Gly; or $X_{21}$ is Ile, Val or Leu, preferably Val; or $X'_{22}$ is Ala, Ser or Gly, preferably Ala; or $X_{23}$ is Ile, Val or Leu, preferably Leu.

Especially preferred are those wherein $X'_1$ is Phe;

$X_2$ is Leu;

$B'_3$ is Arg or Lys;

$X_4$ is Phe;

$X_5$ is Ile;

$U_6$ is Gly;

$U_7$ is Ser or Ala;

$X_8$ is Val;

$X_9$ is Ile;

$B_{10}$ is His;

$X'_{11}$ is Gly or Ala;

$X_{12}$ is Ile;

$U_{13}$ is Gly;

$B_{14}$ is His;

$X_{15}$ is Leu;

$X_{16}$ is Val;

$B^*_{17}$ is His;

$B_{18}$ is His;

$X_{19}$ is Ile, Val or Leu;

$U_{20}$ is Gly, Ser or Ala;

$X_{21}$ is Val;

$X'_{22}$ is Ala;

$X_{23}$ is Leu.

Also especially preferred are the C-terminal amidated forms of the compounds of the invention where the carboxyl terminus is of the formula —CONH$_2$.

Typical compounds within the scope of the clavaspirins are (SEQ ID NO:12 through SEQ ID NO:32):

| FVNFL | GKAIH | AVGHF | VKKLS† | VAL* |
| YFRFL | GKSVH† | SVGRV | IHRVG | LSL* |
| WFHFI | GAIIH | GVGKL | VKHIG | IAL* |
| FLKFL | GGIIK | GIGHV | LHHVS | VAV |
| YVKFI | GAIVH | AVGHV | VKHLG | VSI* |
| WIRFL† | GSIVH† | SIGKL | IHRIS | LGV* |
| FFQFI | GGVIH | GVGRL | VHKIG | VAL* |
| FFRFL | GAIVH | GVGKL | LHHVS | VAL* |
| YVRYL | GSIVH | GVGHL | VRHIG | IAV* |
| SLKFL | GGILK | AVGHV | LKRVG | VGI* |
| YIHFI | GA†ILH | SIGH†L | VHKIG | VSL |
| WIHFL | GSIIR | GVGHI | VHRIS† | IAV* |
| FLRWL | GGILK | GVGRI | LKHIG | LAV* |
| AVRFL | GAIVK | AIGK†V | VHHLG | VGL* |
| GFHFL | GSVIH | SVGHL | IKHVG | ISL* |
| GYKFL | GGVI†H | GIGHL | VHRVS | VGI* |
| AWRFL† | GAIVK | GVAHL | LHKIG | VSI* |
| FLHFI | GSVIH | GIGRL | VKKIG | VAL* |
| YVQ†FI | GGVLK | AVGKL | VHRIG | ISV |
| WIQFL | GAIIH | SIGHI | VRHVG | LAV* |
| GFKFL | GSVIH | GIARV | LHHIG | VAV* |

Also preferred are compounds with the consensus sequence (SEQ ID NO:33):

$F_1L_2B'_3X_4I_5G_6U_7X_8I_9H_{10}U_{11}X_{12}G_{13}B_{14}X_{15}V_{16}B^*_{17}B_{18}X_{19}U_{20}X_{21}U_{22}X_{23}$ wherein $B'_3$, $X_4$, $U_7$, $X_8$, $U_{11}$, $X_{12}$, $B_{14}$, $X_{15}$, $B^*_{17}$, $B_{18}$, $X_{19}$, $U_{20}X_{21}$, $U_{22}$, and $X_{23}$ are as defined above.

Preferred among these are embodiments wherein:

$B_3$ is Arg, His or Lys; or $X_4$ is Phe; or $U_7$ is Ser or Ala; or $X_8$ is Val; or $U_11$ is Gly; or $X_{12}$ is Ile or Val; or $B_{14}$ is His; or $X_{15}$ is Val, Leu or Ile; or $B^*_{17}$ is His; or $B_{18}$ is His; or $X_{19}$ is Val, Leu or Ile; or $U_{20}$ is Gly; or $X_{21}$ is Val, Leu or Ile; or $U_{22}$ is Ala or Ser; or $X_{23}$ is Val, Leu or Ile.

Especially preferred are the embodiments wherein:

$B_3$ is Arg, His or Lys; and $X_4$ is Phe; and $U_7$ is Ser or Ala; and $X_8$ is Val; and $U_{11}$ is Gly; and $X_{12}$ is Ile or Val; and $B_{14}$ is His; and $X_{15}$ is Val, Leu or Ile; and $B^*_{17}$ is His; and $B_{18}$ is His; and $X_{19}$ is Val, Leu or Ile; and $U_{20}$ is Gly; and $X_{21}$ is Val, Leu or Ile; and $U_{22}$ is Ala or Ser; and $X_{23}$ is Val, Leu or Ile.

A particularly preferred form of the compounds of the invention is clavaspirin-1 (SEQ ID NO:41), shown below in comparison with Magainin 1 (SEQ ID NO:34) and Magainin 2 (SEQ ID NO:35) and with clavanins A through E (SEQ ID NO:36 through 40)

| Magainin 1 | ---GI | GKFLH | SAGKF | GKAFV | GEI MKS |
| Magainin 2 | ---GI | GKFLK | SAGKF | GKAFV | NEI MKS |
| Clavanin A | VFQFL | GKIIH | HVGNF | VHGFS | HVF* |
| Clavanin B | VFQFL | GRIIH | HVGNF | VHGFS | HVF* |
| Clavanin C | VFHLL | GKIIH | HVGNF | VY'GFS | HVF* |

| | | | | | |
|---|---|---|---|---|---|
| Clavanin D | AFKLL | GRIIH | HVGNF | VY'GFS | HVF* |
| Clavanin E | LFKLL | GKIIH | HVGNF | VHGFS | HVF* |
| Clavaspirin-1 | FLRFI | GSVIH | GIGHL | VHHIG | VAL* |

*indicates the amide form.

Preparation of the Invention Compounds

The invention compounds, often designated herein "clavaspirins" are essentially peptide backbones which may be modified at the N- or C-terminus and are linear peptides.

Standard methods of synthesis of peptides the size of clavaspirins are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis. Thus, one very practical way -:o obtain the compounds of the invention is to employ these standard chemical synthesis techniques.

In addition to providing the-peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1–6C) as defined above. Similarly, the carboxy terminus may be amidated so as to have the formula —$CONH_2$, —CONHR, or —$CONR_2$, wherein each R is independently hydrocarbyl (1–6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Recombinantly produced forms of the clavaspirins may require subsequent derivatization to modify the N- and/or C-terminus.

For recombinant production, the DNA encoding the clavaspirins of the invention is included in an expression system which places these coding sequences under control of a suitable promoter and other control sequences compatible with an intended host cell. Types of host cells available span almost the entire range of the plant and animal kingdoms. Thus, the clavaspirins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The clavaspirins of the invention can be produced in a form that will result in their secretion from the host cell by fusing to the DNA encoding the clavaspirin, a DNA encoding a suitable signal peptide, or may be produced intracellularly. They may also be produced as fusion proteins with additional amino acid sequence which may or may not need to be subsequently removed prior to the use of these compounds as antimicrobials.

Thus, the clavaspirins of the invention can be produced in a variety of modalities including chemical synthesis and recombinant production or some combination of these techniques.

Any members of the clavaspirin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the clavaspirins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The clavaspirins of the invention in immunogenic form are then injected into a suitable mammalian host and antibody titers in the serum are monitored.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies. The genes encoding monoclonal antibodies secreted by selected hybridomas or other cells may be recovered, manipulated if desired, for example, to provide multiple epitope specificity or to encode a single-chain form and may be engineered for expression in alternative host cells, such as CHO cells.

Thus, as used herein, "antibodies" also includes any immunologically reactive fragment of the immunoglobulins such as Fab, Fab' and $F(ab')_2$ fragments as well as modified immunoreactive forms such as Fv regions, which are produced by manipulation of the relevant genes (isolable, for example, from the appropriate hybridoma).

The antibodies of the invention are, of course, useful in immunoassays for determining the amount or presence of the clavaspirins. Such assays are essential in quality controlled production of compositions containing the clavanins of the invention. In addition, the antibodies can be used to assess the efficacy of recombinant production of the clavaspirins, as well as for screening expression libraries for the presence of clavaspirin encoding genes. They may also be used as affinity ligands for purifying and/or isolating the clavaspirins.

Compositions Containing the Clavaspirins and Methods of Use

The clavaspirins of the invention are effective in inactivating a wide range of microbial, including viral targets, including gram-positive and gram-negative bacteria, yeast, protozoa and certain strains of virus. Accordingly, they can be used in disinfectant compositions and as preservatives for materials such as foodstuffs, cosmetics, medicaments, or other materials containing nutrients for organisms. For use in such contexts, the clavaspirins are supplied either as a single clavaspirin, in admixture with several other clavaspirns or with clavanins, or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the clavaspirins of the invention can be formulated as pharmaceutical or veterinary compositions. Depending on the subject to be treated, the mode of administration, and the type of treatment desired—e.g., prevention, prophylaxis, therapy; the clavaspirins are formulated in ways consonant with these parameters. A summary of such techniques is found in Remington's *Pharmaceutical Sciences*, latest edition, Mack Publishing Co., Easton, Pa.

In general, for use in treatment or prophylaxis, the clavaspirins of the invention may be used alone or in combination with other antibiotics such as erythromycin, tetracycline, macrolides, for example azithromycin and the cephalosporins. Depending on the mode of administration, the clavaspirins will be formulated into suitable compositions to permit facile delivery to the affected areas. Use of the enantiomeric forms containing all D-amino acids may confer advantages such as resistance to those proteases, such as trypsin and chymotrypsin, to which the clavaspirins containing L-amino acids are less resistant.

The clavaspirins of the invention can be administered singly or as mixtures of several clavaspirins or in combination with other pharmaceutically active components, including clavanins and in single or multiple administrations. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The clavaspiriris can be administered also in liposomal compositions or as microemulsions.

If administration is to be oral, the clavaspirins of the invention must be protected from degradation in the stomach using a suitable enteric coating. This may be avoided to some extent by utilizing amino acids in the D-configuration, thus providing resistance to protease. However, the peptide is still susceptible to hydrolysis due to the acidic conditions of the stomach; thus, some degree of enteric coating may still be required.

By appropriately choosing the member of the clavaspirin class of the invention, it is possible to adapt the antimicrobial activity to maximize its effectiveness with respect to a particular target microbe. As used herein, "microbe" will be used to include not only yeast, bacteria, and other unicellular organisms, but also viruses. The particular clavaspirins can also be chosen to be advantageous in a particular context, such as low salt or physiological salt, the presence or human serum, or conditions that mimic the conditions found in blood and tissue fluids.

Since certain forms of the clavaspirins are enhanced in effectiveness at reduced pH (i.e., those wherein histidine represents several of the basic residues, these forms can advantageously be used in low pH environments such as the stomach or sites of inflammation.

The clavaspirins of the invention may also be applied to plants or to their environment to prevent microbial-induced including viral diseases in these plants. Suitable compositions for this use will typically contain a diluent as well as a spreading agent or other ancillary agreements beneficial to the plant or to the environment.

Thus, the clavaspirins of the invention may be used in any context wherein an antimicrobial action is required. This use may be an entirely in vitro use, or the peptides may be administered to organisms.

In addition, the antimicrobial, including antiviral activity may be generated in situ by administering an expression system suitable for the production of the clavaspirins of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

The following examples are intended to illustrate but not to limit the invention.

EXAMPLE 1

Preparation of Clavanins A–D from *S. clava*

Clavanins A–D were isolated from tunics of Styela clava in batches of 50, obtained from Marinus Biologicals, Long Beach, Calif. and found to have the structures (SEQ ID NO:39):

| Clavanin A | VFQFL | GKIIH | HVGNF | VHGFS | HVF* |
| Clavanin B | VFQFL | GRIIH | HVGNF | VHGFS | HVF* |
| Clavanin C | VFHLL | GKIIH | HVGNF | VY'GFS | HVF* |
| Clavanin D | AFKLL | GRIIH | HVGNF | VY'GFS | HVF* |

Y' indicates a modified tyrosine residue, in this case, o-methyl tyrosine. The * indicates amidation.

EXAMPLE 2

Recovery of Clavanin-Encoding cDNA

Total RNA from tunicate pharyngeal tissues was isolated and purified using a total RNA separator kit (Clontech, Palo Alto, Calif.). First strand cDNA synthesis and clavanin 3' side cDNA amplification were carried out with a 3'RACE kit (Gibco BRL, Gaithersburg, Md.) using 1 μg of total pharyngeal RNA, and 10 μM adapter primer to obtain the first strand of cDNA. A degenerate 30-base primer (SEQ ID NO:42), 5'-<u>GTCGACTAGT</u>CAYCAYGTIGGIAAYTT YGT-3', where Y represents T or C, I represents inosine, and the single underlining indicates a Spe I restriction site that corresponded to amino acids 11–17 of clavanins A (SEQ ID NO:36), B (SEQ ID NO:37), C (SEQ ID NO:38), and D (SEQ ID NO:39) (His-His-Val-Gly-Asn-Phe-Val) was designed.

PCR was performed in a total volume of 50 μl that contained: ⅒ vol. of first strand cDNA, 10 pmol each of degenerate primer and AUAP primer, and 5 U of pfu DNA polymerase. The reaction was run for 35 cycles, with 1 min denaturation (94° C.), 1 min annealing (48° C.), and 2.5 min extension (72° C.) per cycle. PCR product about 250 bp in size was cloned into pCRScript SK vector (Stratagene, La Jolla, Calif.). DNA sequencing results confirmed that it was the 3' side cDNA sequence of clavanin.

To obtain a DNA library, pharyngeal tissues (the functional equivalent of bone marrow in tunicates) were removed from live Styela clava and stored at −70° C. A custom cDNA library was constructed for us in λTripIEx™ by Clontech Laboratories. E. coli stain XL1-Blue was used as a host, and phage plaques DNA was transferred to nylon membranes (Dupont, Boston, Mass.). The filters were hybridized with $^{32}$P-labeled 250 bp clavanin 3' side cDNA, as per the above. Hybridization was carried out at 50° C. overnight with Rapid-hyb buffer (Amersham). The filters were washed several times, finally at 60° C. in 0.1×SSC and 0.1% SDS, and exposed to X-ray film with an intensifying screen at −70° C. Positive clones were subjected to one or two additional rounds of plaque screening at low density. Finally, 50 positive clones were identified from approximately $1.2 \times 10^5$ clones.

To obtain DNA sequence, λ phage DNA was purified using a Lamda kit (AIAGEN, Chatsworth, Calif.). The purified DNA or picked plaques were subjected to long-distance PCR using LD-Insert Screening Amplimers (Clontech Lab., Palo Alto, Calif.). PCR amplification was performed according to the manufacturer's protocol. The PCR products of inserts were purified from low melting agarose gel, and sequenced directly by fluoresceinlabeled dideoxynucleotide terminator method, and the sequencing reaction were analyzed on an Applied Biosystems 373 DNA Sequencer (Perkin-Elmer, Palo Alto, Calif.). Of the 26 clones sequenced to date, we have found 3 clavanin A, 12 clavanin C, 7 clavanin D, 2 clavanin E, and 2 clavaspirin-1. The sequence of each precursor is shown in FIGS. 1A–1E.

The 5'-cDNA inserts contain a short untranslated part (≈20 bp). The cDNA for clavaspirin (and the clavanins) contains a open reading frame of 240 base pairs that encodes an 80-amino acid :residue prepropeptide containing a typical 19-amino acid signal sequence, followed by a short, hydrophobic propiece LEERKSEEEK (SEQ ID NO:43) with a net negative charge. A glycine residue follows the amino acids present in the mature clavanins and clavaspirins, as expected for amidated peptides. Finally, there are 27 amino acids that follow the mature clavanin or clavaspirin + glycine sequence. (See FIG. 1F)

Thus, the clavanins and clavaspirins are encoded as C-terminal extended propeptides; post-translational processing removes the C-terminal 27 amino acids and amidates the residual peptide chain.

FIG. 2 shows a comparison of the coding sequences of clavanin C with clavaspirin-1 as shown in FIG. 2, extensive hormology is found at the nucleotide sequence level.

Clavaspirin-1 is an amphipathic protein, as is shown by its helical wheel projection in FIG. 3. This diagram was drawn with the "helwheel" program of PC-Gene (Intelligenetics).

EXAMPLE 3

Antimicrobial Activity of the Clavaspirins

Clavaspirin-1, prepared synthetically, was tested for antimicrobial activity in the radial diffusion assays described by Lehrer, R. et al. *J Immunol Meth* (1991) 137:167–173. In all cases, the underlay gels contained 1% w/v agarose and 10 mM phosphate/citrate buffer (9:1 phosphate:citrate ratio) and a 1:100 dilution of trypticase soy broth (TSB) which corresponds to a final concentration of 0.3 mg TSB powder/ 100 underlay agar. The final pH of the underlay agars was adjusted as described in individual experiments, as was the sodium chloride concentration. Control peptides included clavanin A, magainin 1 (Bachem) and cecropin P1 (Sigma). Magainin 1 and clavanin A have the aminc acid sequence described hereinabove; the primary sequence of cecropin P1 is described in Lee, J. Y. et al. *Proc Natl Acad Sci USA* (1989) 86:9159–9162.

Figures 5A, 5B, 5C:
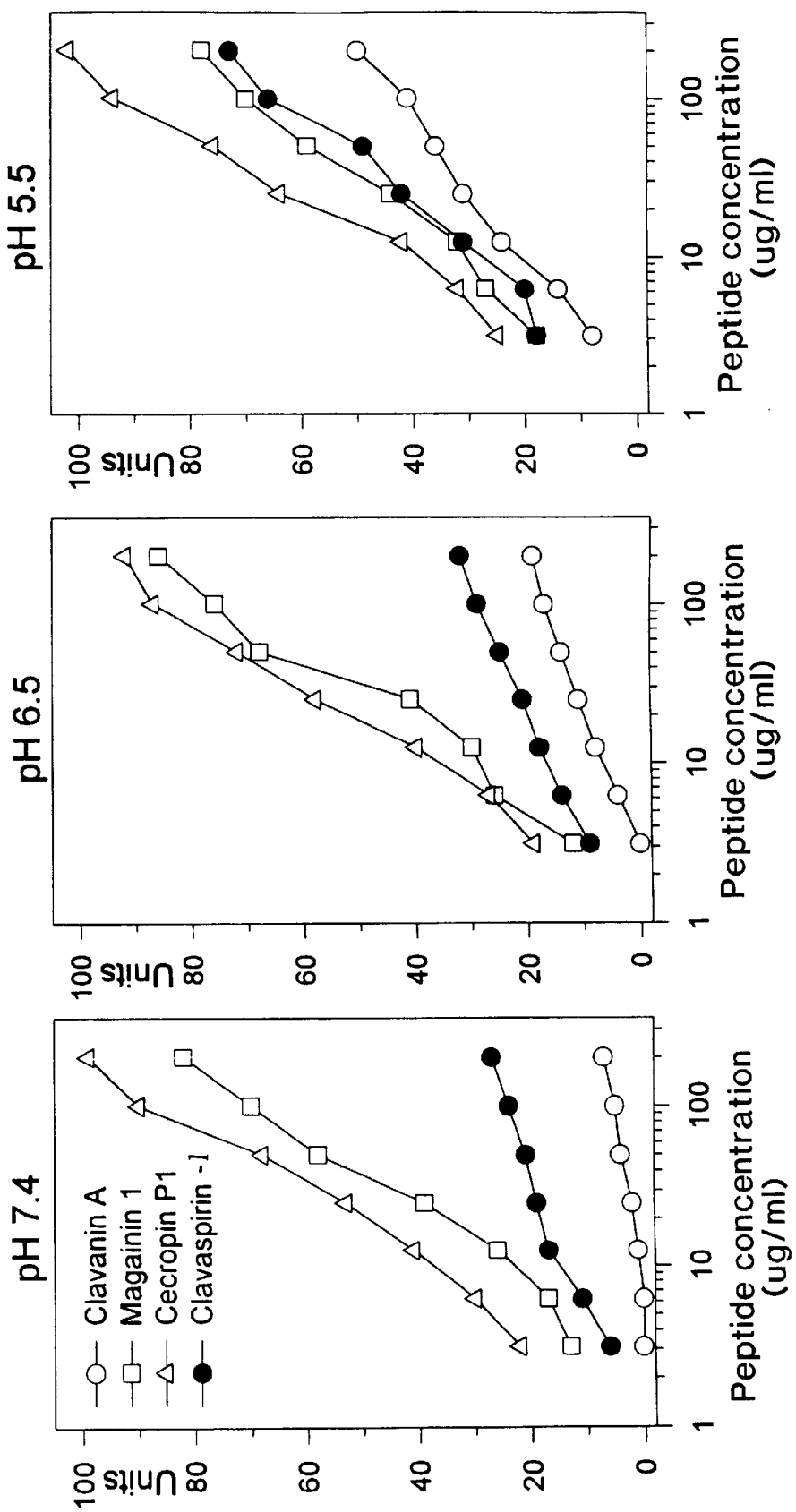
FIGS. 5A–5C show the antimicrobial activity of clavaspirin-1 against *E. coli* ML-35p at various pHs.

FIGS. 4, 5 and 6 describe the results of this assay when the target organism is *Listeria monocytogenes, Escherichia coli* ML-35p, or *Candida albicans*, respectively where each target of the activity was tested at pH7.4, pH6.5 and pH5.5.

As shown, the various peptides tested were affected in their activity by different ways with changing pH depending on the target. When *L. monocytogenes* was the target, clavaspirin-1 showed the greatest activity at pH5.5 and lost some activity at high concentrations, as did clavanin A, when the pH was lowered. A similar effect is seen with respect to activity against *E. coli* ML-35p. All of the peptides tested showed this effect when the target was *C. albicans*.

Figures 9A, 9B, 9C, 9D:
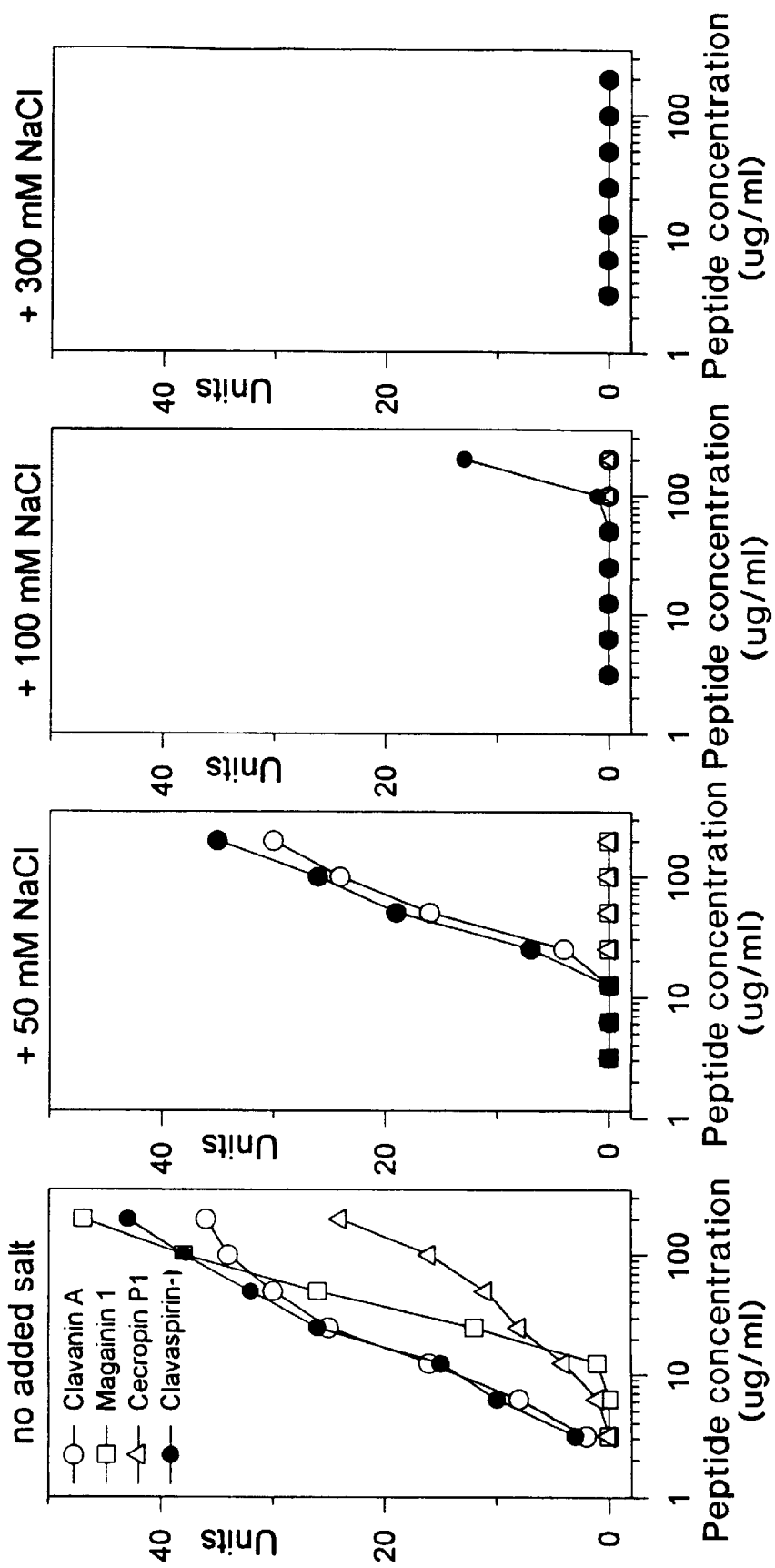
FIGS. 9A–9D show the antimicrobial activity of clavaspirin-1 against *C. albicans* at various salt concentrations.

FIGS. 7, 8 and 9 show the results against the same targets using the same peptides at varying salt concentrations. Against *L. monocytogenes* (FIG. 7) clavaspirin-1 shows the best retention of activity of all the peptides tested with increasing salt concentration. Similar results are obtained when *E. coli* is the target (FIG. 8). As shown in FIG. 9, although both clavanin A and clavaspirin-1 retain most activity at 50 mM sodium chloride, all of the peptides tested became inactive at salt concentrations of 100 mM or 300 mM. The resistance to high salt concentrations shown by clavaspirin-1 is important as blood and tissue fluids typically have sodium and chloride concentrations of 100–140 mM. (Because blood and tissue fluids contain about 25 mM bicarbonate, the sodium concentration s always higher than the chloride concentration.)

Figure 10A:
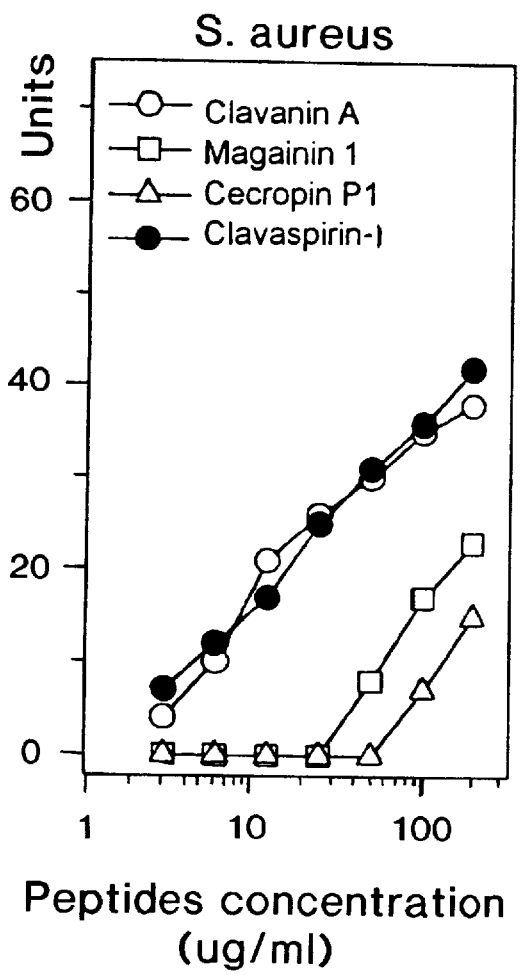
FIGS. 10A and 10B show the antimicrobial activity of clavaspirin-1 against *Staphylococcus aureus* and *Pseudomonas auruginosa*, respectively.
Figure 10B:
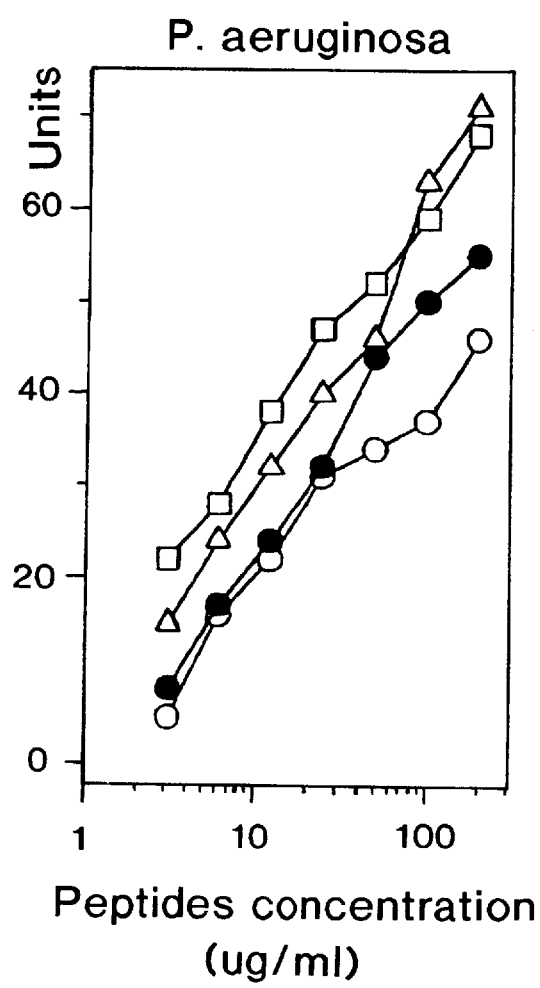

FIG. 10 shows the results of similar assays conducted at pH5.5 against *Staphylococcus aureus* and *Pseudomonas auruginosa*. The activity of both clavaspirin-1 and clavanin A with respect to *S. aureus* is demonstrably better than that of magainin 1 or cecropin P1. All four peptides tested were comparably active against *P. auruginosa*.

We claim:

1. A compound in purified and isolated form, having antimicrobial activity of the formula (SEQ ID NO:1)

$$X'_1X_2B'_3X_4X_5U_6U_7X_8X_9B_{10}X'_{11}X_{12}U_{13}B_{14}X_{15}X_{16}B^*_{17}B_{18}X_{19}U_{20}X_{21}X'_{22}X_{23} \quad (1)$$

including the salts, esters, amides and acylated forms thereof
wherein
    $X'_1$ is Phe, Trp, Tyr, or Ala; and
    $X_2$ is Val, Leu, Ile, Phe, Trp or Tyr; and
    $B'_3$ is Asn, Gln, His, Lys or Arg; and
    $X_4$ and $X_5$ is each independently selected from the group consisting of Phe, Leu, Tyr, Ile and Val; and
    $U_6$ is Gly, Ser or Ala; and
    $U_7$ Gly, Ser or Ala; and
    $X_8$ and $X_9$ is each independently selected from the group consisting of Ile, Leu and Val; and
    $B_{10}$ is His, Lys or Arg; and
    $X'_{11}$ is Ala, Ser or Gly; and
    $X_{12}$ is Val, Ile or Leu; and
    $U_{13}$ is Ala, Ser or Gly; and
    $B_{14}$ is Arg, Lys or His; and
    $X_{15}$ and $X_{16}$ is each independently selected from the group consisting of Val, Leu and Ile; and
    $B^*_{17}$ is His, Lys, Arg, Trp, Phe or Tyr or a modified form thereof; and
    $B_{18}$ is Arg, Lys or His; and
    $X_{19}$ is Leu, Ile or Val; and
    $U_{20}$ is Gly, Ala or Ser; and
    $X_{21}$ is Ile, Val or Leu; and
    $X'_{22}$ is Ala, Ser or Gly; and
    $X_{23}$ is Ile, Val or Leu.

2. The compound of claim 1 wherein at least one amino acid residue is in the D configuration.

3. The compound of claim 1 wherein at least one bond between two amino acid residues is a peptide bond mimic.

4. The compound of claim 1 wherein
    $X'_1$ is Phe; and
    $X_2$ is Leu; and
    $B'_3$ is Arg or Lys; and
    $X_4$ is Phe; and
    $X_5$ is Ile; and
    $U_6$ is Gly; and
    $U_7$ is Ser or Ala; and
    $X_8$ is Val; and
    $X_9$ is Ile; and
    $B_{10}$ is His; and
    $X'_{11}$ is Gly or Ala; and
    $X_{12}$ is Ile; and
    $U_{13}$ is Gly; and
    $B_{14}$ is His; and
    $X_{15}$ is Leu; and
    $X_{16}$ is Val; and
    $B^*_{17}$ is His; and
    $B_{18}$ is His; and
    $X_{19}$ is Ile, Val or Leu; and
    $U_{20}$ is Gly, Ser or Ala; and
    $X_{21}$ is Val; and
    $X'_{22}$ is Ala; and
    $X_{23}$ is Leu.

5. The compound of claim 1 which has the formula (SEQ ID NO:33):

$$F_1L_2B'_3X_4I_5G_6U_7X_8I_9H_{10}U_{11}X_{12}G_{13}B_{14}X_{15}V_{16}B^*_{17}B_{18}X_{19}U_{20}X_{21}U_{22}X_{23}$$

wherein
    $B_3$ is Arg, His or Lys; and
    $X_4$ is Phe; and
    $U_7$ is Ser or Ala; and
    $X_8$ is Val; and
    $U_{11}$ is Gly; and
    $X_{12}$ is Ile or Val; and
    $B_{14}$ is His; and
    $X_{15}$ is Val, Leu or Ile; and
    $B^*_{17}$ is His; and
    $B_{18}$ is His; and
    $X_{19}$ is Val, Leu or Ile; and
    $U_{20}$ is Gly; an
    $X_{21}$ is Val, Leu or Ile; and
    $U_{22}$ is Ala or Ser; and
    $X_{23}$ is Val, Leu or Ile.

6. The compound of claim 5 which is (SEQ ID NO:41):
    Clavaspirin-1 F: FLRFIGSVIHGIGHLVHHIGVAL and the amidated forms thereof.

7. A peptide of formula (1) in purified and isolated form, having antimicrobial activity, which is isolable from a tunicate wherein formula (1) is $$X'_1X_2B'_3X_4X_5U_6U_7X_8X_9B_{10}X'_{11}X_{12}U_{13}B_{14}X_{15}X_{16}B^*_{17}B_{18}X_{19}U_{20}X_{21}X'_{22}X_{23} \quad \text{(SEQ ID NO:1)}$$

wherein X is a hydrophobic amino acid residue, X' is a small or hydrophobic amino acid residue, B is a basic amino acid residue, B' is a basic or polar/large amino acid residue, B* is a basic or hydrophobic amino acid residue, and U is a small amino acid residue.

8. A pharmaceutical composition for antimicrobial use which comprises the compound of claim 1 in admixture with at least one pharmaceutically acceptable excipient.

9. A composition for application to plants or plant environments for conferring resistance to fungal, bacterial or viral infection in plants which comprises the compound of claim 1 in admixture with at least one environmentally acceptable diluent.

10. A method to prevent the growth of a virus or bacterium or fungus which method comprises contacting a material which supports the growth of said virus or bacterium or fungus with an amount of the compound of claim 1 effective to prevent said growth, or with a composition containing the compound of claim 1 as active ingredient.

11. The compound of claim 5 wherein at least one amino acid residue is in the D configuration.

12. The compound of claim 5 wherein at least one bond between two amino acid residues is a peptide bond mimic.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
       (A) LENGTH: 23 amino acids
       (B) TYPE: amino acid
       (C) STRANDEDNESS: single
       (D) TOPOLOGY: linear (xi) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa
            20

(2) INFORMATION FOR SEQ ID NO:2:

(i) SEQUENCE CHARACTERISTICS:
       (A) LENGTH: 381 base pairs
       (B) TYPE: nucleic acid
       (C) STRANDEDNESS: double
       (D) TOPOLOGY: linear (ix) FEATURE:
       (A) NAME/KEY: Coding Sequence
       (B) LOCATION: 18...257
       (D) OTHER INFORMATION:
       (A) NAME/KEY: polyA_site
       (B) LOCATION: 381...0
       (D) OTHER INFORMATION:

(xi) SEQUENCE DESCRIPTION: SEQ ID NO:2:

```
GACAAACAAC AGGAAAG ATG AAA ACA ACA ATT TTG ATT CTT CTC ATA CTG        50
                  Met Lys Thr Thr Ile Leu Ile Leu Leu Ile Leu
                   1               5                   10

GGA CTT GGC ATC AAT GCA AAA TCT CTG GAG GAA AGA AAA TCG GAG GAA        98
Gly Leu Gly Ile Asn Ala Lys Ser Leu Glu Glu Arg Lys Ser Glu Glu
             15                  20                  25

GAG AAA GTA TTC CAA TTC CTT GGC AAA ATT ATT CAT CAT GTT GGC AAT       146
Glu Lys Val Phe Gln Phe Leu Gly Lys Ile Ile His His Val Gly Asn
                 30                  35                  40

TTT GTA CAT GGT TTT AGC CAC GTG TTC GGC GAC GAC CAA CAA GAT AAT       194
Phe Val His Gly Phe Ser His Val Phe Gly Asp Asp Gln Gln Asp Asn
         45                  50                  55

GGA AAG TTT TAT GGC CAC TAC GCA GAA GAC AAT GGC AAG CAT TGG TAT       242
Gly Lys Phe Tyr Gly His Tyr Ala Glu Asp Asn Gly Lys His Trp Tyr
 60                  65                  70                  75

GAT ACC GGG GAT CAA TAAAAAAGTT TTAAACAGCT ACGCGACTTG AAGACGGACG G     298
Asp Thr Gly Asp Gln
                 80

ACCCGGCAGA ACATTGATAT TTCTTGTTTT CTTTGATTAA AGGCTAGCCT TATTACTCAG    358

AATATAACAC TACATTGCAT TCA                                            381
```

(2) INFORMATION FOR SEQ ID NO:3:

(i) SEQUENCE CHARACTERISTICS:
       (A) LENGTH: 80 amino acids
       (B) TYPE: amino acid
       (C) STRANDEDNESS: single
       (D) TOPOLOGY: linear (ii) MOLECULE TYPE: protein (v) FRAGMENT TYPE: internal (xi) SEQUENCE DESCRIPTION: SEQ ID NO:3:

```
Met Lys Thr Thr Ile Leu Ile Leu Leu Ile Leu Gly Leu Gly Ile Asn
1               5                   10                  15

Ala Lys Ser Leu Glu Glu Arg Lys Ser Glu Glu Glu Lys Val Phe Gln
            20                  25                  30

Phe Leu Gly Lys Ile Ile His His Val Gly Asn Phe Val His Gly Phe
                35                  40                  45

Ser His Val Phe Gly Asp Asp Gln Gln Asp Asn Gly Lys Phe Tyr Gly
    50                  55                  60

His Tyr Ala Glu Asp Asn Gly Lys His Trp Tyr Asp Thr Gly Asp Gln
65              70                  75                  80
```

(2) INFORMATION FOR SEQ ID NO:4:

(i) SEQUENCE CHARACTERISTICS:
        (A) LENGTH: 389 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 26...265
        (D) OTHER INFORMATION:
        (A) NAME/KEY: polyA_site
        (B) LOCATION: 389...0
        (D) OTHER INFORMATION:

(xi) SEQUENCE DESCRIPTION: SEQ ID NO:4:

```
CAAACTCAGA CAAACAACAG GAAAG ATG AAA ACA ACA ATT TTG ATT CTT CTC        52
                           Met Lys Thr Thr Ile Leu Ile Leu Leu
                           1               5

ATA CTG GGA CTT GGC ATC AAT GCA AAA TCT CTG GAG GAA AGA AAA TCG       100
Ile Leu Gly Leu Gly Ile Asn Ala Lys Ser Leu Glu Glu Arg Lys Ser
10                  15                  20                  25

GAG GAA GAA AAA GTA TTC CAT CTC CTT GGC AAA ATT ATT CAT CAT GTT       148
Glu Glu Glu Lys Val Phe His Leu Leu Gly Lys Ile Ile His His Val
                30                  35                  40

GGC AAT TTT GTA TAT GGT TTT AGC CAC GTG TTC GGC GAC GAC CAA CAA       196
Gly Asn Phe Val Tyr Gly Phe Ser His Val Phe Gly Asp Asp Gln Gln
                45                  50                  55

GAT AAT GGA AAG TTT TAT GGC CAC TAC GCA GAA GAC AAT GGC AAG CAT       244
Asp Asn Gly Lys Phe Tyr Gly His Tyr Ala Glu Asp Asn Gly Lys His
            60                  65                  70

TGG TAT GAT ACC GGG GAT CAA TAAAAAAGTT TTAAACAGCT ACGCGACTTG AAGA     299
Trp Tyr Asp Thr Gly Asp Gln
75              80

CGGACGGACC CGGCAGAACA TTGATATTTC TTGTTTTCTT TGATTAAAGG CTAGCCTTAT     359

TACTCAGAAT ATAACACTAC ATTGCATTCA                                      389
```

(2) INFORMATION FOR SEQ ID NO:5:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:5:

| Met | Lys | Thr | Thr | Ile | Leu | Ile | Leu | Leu | Ile | Leu | Gly | Leu | Gly | Ile | Asn |
|---|---|---|---|---|---|---|---|---|---|---|---|---|---|---|---|
| 1 | | | | 5 | | | | | 10 | | | | | 15 | |

| Ala | Lys | Ser | Leu | Glu | Glu | Arg | Lys | Ser | Glu | Glu | Lys | Val | Phe | His |
|---|---|---|---|---|---|---|---|---|---|---|---|---|---|---|
| | | | 20 | | | | | 25 | | | | | 30 | |

| Leu | Leu | Gly | Lys | Ile | Ile | His | His | Val | Gly | Asn | Phe | Val | Tyr | Gly | Phe |
|---|---|---|---|---|---|---|---|---|---|---|---|---|---|---|---|
| | | | 35 | | | | | 40 | | | | | 45 | | |

| Ser | His | Val | Phe | Gly | Asp | Asp | Gln | Gln | Asp | Asn | Gly | Lys | Phe | Tyr | Gly |
|---|---|---|---|---|---|---|---|---|---|---|---|---|---|---|---|
| | 50 | | | | | 55 | | | | | 60 | | | | |

| His | Tyr | Ala | Glu | Asp | Asn | Gly | Lys | His | Trp | Tyr | Asp | Thr | Gly | Asp | Gln |
|---|---|---|---|---|---|---|---|---|---|---|---|---|---|---|---|
| 65 | | | | | 70 | | | | | 75 | | | | | 80 |

(2) INFORMATION FOR SEQ ID NO:6:

(i) SEQUENCE CHARACTERISTICS:
        (A) LENGTH: 389 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 26...265
        (D) OTHER INFORMATION:
        (A) NAME/KEY: polyA_site
        (B) LOCATION: 389...0
        (D) OTHER INFORMATION:

(xi) SEQUENCE DESCRIPTION: SEQ ID NO:6:

```
CAAACTCAGA CAAACAACAG GAAAG ATG AAA ACA ACA ATT TTG ATT CTT CTC           52
                           Met Lys Thr Thr Ile Leu Ile Leu Leu
                            1               5

ATA CTG GGA CTT GGC ATC AAT GCA AAA TCT CTG GAG GAA AGA AAA TCG          100
Ile Leu Gly Leu Gly Ile Asn Ala Lys Ser Leu Glu Glu Arg Lys Ser
 10              15                  20                  25

GAG GAA GAG AAA GCT TTC AAA CTC CTT GGC AGA ATT ATT CAT CAT GTT          148
Glu Glu Glu Lys Ala Phe Lys Leu Leu Gly Arg Ile Ile His His Val
                30                  35                  40

GGC AAT TTT GTA TAT GGT TTT AGC CAC GTG TTC GGC GAC GAC CAA CAA          196
Gly Asn Phe Val Tyr Gly Phe Ser His Val Phe Gly Asp Asp Gln Gln
                45                  50                  55

GAT AAT GGA AAG TTT TAT GGC CAC TAC GCA GAA GAC AAT GGC AAG CAT          244
Asp Asn Gly Lys Phe Tyr Gly His Tyr Ala Glu Asp Asn Gly Lys His
                60                  65                  70

TGG TAT GAT ACC GGG GAT CAA TAAAAAGTT TTAAACAGCT ACGCGACTTG AAGA         299
Trp Tyr Asp Thr Gly Asp Gln
 75              80

CGGACGGACC CGGCAGAACA TTGATATTTC TTGTTTTCTT TGATTAAAGG CTAGCCTTAT        359

TACTCAGAAT ATAACACTAC ATTGCATTCA                                         389
```

(2) INFORMATION FOR SEQ ID NO:7:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:7:

```
Met Lys Thr Thr Ile Leu Ile Leu Leu Ile Leu Gly Leu Gly Ile Asn
1               5                   10                  15

Ala Lys Ser Leu Glu Glu Arg Lys Ser Glu Glu Lys Ala Phe Lys
        20                  25                  30

Leu Leu Gly Arg Ile Ile His His Val Gly Asn Phe Val Tyr Gly Phe
        35                  40                  45

Ser His Val Phe Gly Asp Asp Gln Gln Asp Asn Gly Lys Phe Tyr Gly
    50                  55                  60

His Tyr Ala Glu Asp Asn Gly Lys His Trp Tyr Asp Thr Gly Asp Gln
65              70                  75                  80
```

(2) INFORMATION FOR SEQ ID NO:8:

(i) SEQUENCE CHARACTERISTICS:
        (A) LENGTH: 389 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 26...265
        (D) OTHER INFORMATION:
        (A) NAME/KEY: polyA_site
        (B) LOCATION: 389...0
        (D) OTHER INFORMATION:

(xi) SEQUENCE DESCRIPTION: SEQ ID NO:8:

```
CAAACTCAGA CAAACAACAG GAAAG ATG AAA ACA ACA ATT TTG ATT CTT CTC          52
                           Met Lys Thr Thr Ile Leu Ile Leu Leu
                           1               5

ATA CTG GGA CTT GGC ATC AAT GCA AAA TCT CTG GAG GAA AGA AAA TCG         100
Ile Leu Gly Leu Gly Ile Asn Ala Lys Ser Leu Glu Glu Arg Lys Ser
10              15                  20                  25

GAG GAA GAG AAA TTA TTC AAA CTC CTT GGC AAA ATT ATT CAT CAT GTT         148
Glu Glu Glu Lys Leu Phe Lys Leu Leu Gly Lys Ile Ile His His Val
                30                  35                  40

GGC AAT TTT GTA CAT GGT TTT AGC CAC GTG TTC GGC GAC GAC CAA CAA         196
Gly Asn Phe Val His Gly Phe Ser His Val Phe Gly Asp Asp Gln Gln
            45                  50                  55

GAT AAT GGA AAG TTT TAT GGC TAC TAC GCA GAA GAC AAT GGC AAG CAT         244
Asp Asn Gly Lys Phe Tyr Gly Tyr Tyr Ala Glu Asp Asn Gly Lys His
        60                  65                  70

TGG TAT GAT ACC GGG GAT CAA TAAAAAGTT TTAAACAGCT ACGCGACTTG AAGA        299
Trp Tyr Asp Thr Gly Asp Gln
75              80

CGGACGGACC CGGCAGAACA TTGATATTTC TTGTTTTCTT TGATTAAAGG CTAGCCTTAT       359

TACTCAGAAT ATAACACTAC ATTGCATTCA                                        389
```

(2) INFORMATION FOR SEQ ID NO:9:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:9:

```
Met Lys Thr Thr Ile Leu Ile Leu Leu Ile Leu Gly Leu Gly Ile Asn
1               5                   10                  15
```

```
Ala Lys Ser Leu Glu Glu Arg Lys Ser Glu Glu Lys Leu Phe Lys
         20                  25                  30

Leu Leu Gly Lys Ile Ile His His Val Gly Asn Phe Val His Gly Phe
             35                  40                  45

Ser His Val Phe Gly Asp Asp Gln Gln Asp Asn Gly Lys Phe Tyr Gly
 50                  55                  60

Tyr Tyr Ala Glu Asp Asn Gly Lys His Trp Tyr Asp Thr Gly Asp Gln
 65                  70                  75                  80

(2) INFORMATION FOR SEQ ID NO:10:

(i) SEQUENCE CHARACTERISTICS:
        (A) LENGTH: 391 base pairs
        (B) TYPE: nucleic acid
        (C) STRANDEDNESS: double
        (D) TOPOLOGY: linear (ix) FEATURE:
        (A) NAME/KEY: Coding Sequence
        (B) LOCATION: 28...267
        (D) OTHER INFORMATION:
        (A) NAME/KEY: polyA_site
        (B) LOCATION: 391...0
        (D) OTHER INFORMATION:

(xi) SEQUENCE DESCRIPTION: SEQ ID NO:10:

ATCAAACTCA GACAAACAAC AGGAAAG ATG AAA ACA ATA ATT TTG ATT CTA CTC      54
                             Met Lys Thr Ile Ile Leu Ile Leu Leu
                              1               5

ATA TTG GGA CTT GGC ATC GAT GCA AAA TCC CTG GAG GAA AGC AAA GCG       102
Ile Leu Gly Leu Gly Ile Asp Ala Lys Ser Leu Glu Glu Ser Lys Ala
 10              15                  20                  25

GAC GAA GAG AAA TTC CTC CGT TTC ATT GGC AGC GTT ATA CAT GGT ATT       150
Asp Glu Glu Lys Phe Leu Arg Phe Ile Gly Ser Val Ile His Gly Ile
                 30                  35                  40

GGA CAC CTT GTA CAT CAT ATT GGC GTC GCA TTA GGC GAC GAC CAA CAA       198
Gly His Leu Val His His Ile Gly Val Ala Leu Gly Asp Asp Gln Gln
             45                  50                  55

GAT AAT GGA AAG TTT TAT GGC TAC TAC GCA GAA GAC AAT GGC AAG CAT       246
Asp Asn Gly Lys Phe Tyr Gly Tyr Tyr Ala Glu Asp Asn Gly Lys His
         60                  65                  70

TGG TAT GAT ACC GGG GAT CAA TAAAAAAGTT TTAAACAGCT ACGCGACTTG AAGA     301
Trp Tyr Asp Thr Gly Asp Gln
     75                  80

CGGACGGACC CGGCAGAACA TTGATATTTC TTGTTTTCTT TGATTAAAGG CTAGCCTTAT     361

TACTCAGAAT ATAACACTAC ATTGCATTCA                                      391

(2) INFORMATION FOR SEQ ID NO:11:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:11:

Met Lys Thr Ile Ile Leu Ile Leu Leu Ile Leu Gly Leu Gly Ile Asp
 1               5                  10                  15

Ala Lys Ser Leu Glu Glu Ser Lys Ala Asp Glu Glu Lys Phe Leu Arg
             20                  25                  30
```

```
Phe Ile Gly Ser Val Ile His Gly Ile Gly His Leu Val His His Ile
         35                  40                  45

Gly Val Ala Leu Gly Asp Asp Gln Gln Asp Asn Gly Lys Phe Tyr Gly
 50                  55                  60

Tyr Tyr Ala Glu Asp Asn Gly Lys His Trp Tyr Asp Thr Gly Asp Gln
 65                  70                  75                  80
```

(2) INFORMATION FOR SEQ ID NO:12:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: None (ix) FEATURE:
       (A) NAME/KEY: Other
       (B) LOCATION: 20...0
       (D) OTHER INFORMATION: D-Ser (xi) SEQUENCE DESCRIPTION: SEQ ID NO:12:

```
Phe Val Asn Phe Leu Gly Lys Ala Ile His Ala Val Gly His Phe Val
 1               5                  10                  15

Lys Lys Leu Xaa Val Ala Leu
              20
```

(2) INFORMATION FOR SEQ ID NO:13:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: None (ix) FEATURE:
       (A) NAME/KEY: Other
       (B) LOCATION: 10...0
       (D) OTHER INFORMATION: D-His (xi) SEQUENCE DESCRIPTION: SEQ ID NO:13:

```
Tyr Phe Arg Phe Leu Gly Lys Ser Val Xaa Ser Val Gly Arg Val Ile
 1               5                  10                  15

His Arg Val Gly Leu Ser Leu
              20
```

(2) INFORMATION FOR SEQ ID NO:14:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:14:

```
Trp Phe His Phe Ile Gly Ala Ile Ile His Gly Val Gly Lys Leu Val
 1               5                  10                  15

Lys His Ile Gly Ile Ala Leu
              20
```

(2) INFORMATION FOR SEQ ID NO:15:

(i) SEQUENCE CHARACTERISTICS:

(A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

Phe Leu Lys Phe Leu Gly Gly Ile Ile Lys Gly Ile Gly His Val Leu
1               5                   10                  15

His His Val Ser Val Ala Val
            20

(2) INFORMATION FOR SEQ ID NO:16:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

Tyr Val Lys Phe Ile Gly Ala Ile Val His Ala Val Gly His Val Val
1               5                   10                  15

Lys His Leu Gly Val Ser Ile
            20

(2) INFORMATION FOR SEQ ID NO:17:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 5...0
        (D) OTHER INFORMATION: D-Leu
        (A) NAME/KEY: Other
        (B) LOCATION: 10...0
        (D) OTHER INFORMATION: D-His (xi) SEQUENCE DESCRIPTION: SEQ ID NO:17:

Trp Ile Arg Phe Xaa Gly Ser Ile Val Xaa Ser Ile Gly Lys Leu Ile
1               5                   10                  15

His Arg Ile Ser Leu Gly Val
            20

(2) INFORMATION FOR SEQ ID NO:18:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

Phe Phe Gln Phe Ile Gly Gly Val Ile His Gly Val Gly Arg Leu Val
1               5                   10                  15

His Lys Ile Gly Val Ala Leu
            20

(2) INFORMATION FOR SEQ ID NO:19:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

```
Phe Phe Arg Phe Leu Gly Ala Ile Val His Gly Val Gly Lys Leu Leu
 1               5                  10                  15
His His Val Ser Val Ala Leu
                 20
```

(2) INFORMATION FOR SEQ ID NO:20:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

```
Tyr Val Arg Tyr Leu Gly Ser Ile Val His Gly Val Gly His Leu Val
 1               5                  10                  15
Arg His Ile Gly Ile Ala Val
                 20
```

(2) INFORMATION FOR SEQ ID NO:21:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:21:

```
Ser Leu Lys Phe Leu Gly Gly Ile Leu Lys Ala Val Gly His Val Leu
 1               5                  10                  15
Lys Arg Val Gly Val Gly Ile
                 20
```

(2) INFORMATION FOR SEQ ID NO:22:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 7...0
        (D) OTHER INFORMATION: D-Ala
        (A) NAME/KEY: Other
        (B) LOCATION: 14...0
        (D) OTHER INFORMATION: D-His (xi) SEQUENCE DESCRIPTION: SEQ ID NO:22:

```
Tyr Ile His Phe Ile Gly Xaa Ile Leu His Ser Ile Gly Xaa Leu Val
 1               5                  10                  15
```

```
His Lys Ile Gly Val Ser Leu
            20

(2) INFORMATION FOR SEQ ID NO:23:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 20...0
        (D) OTHER INFORMATION: D-Ser (xi) SEQUENCE DESCRIPTION: SEQ ID NO:23:

Trp Ile His Phe Leu Gly Ser Ile Ile Arg Gly Val Gly His Ile Val
1               5                   10                  15

His Arg Ile Xaa Ile Ala Val
            20

(2) INFORMATION FOR SEQ ID NO:24:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Phe Leu Arg Trp Leu Gly Gly Ile Leu Lys Gly Val Gly Arg Ile Leu
1               5                   10                  15

Lys His Ile Gly Leu Ala Val
            20

(2) INFORMATION FOR SEQ ID NO:25:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 14...0
        (D) OTHER INFORMATION: D-Lys (xi) SEQUENCE DESCRIPTION: SEQ ID NO:25:

Ala Val Arg Phe Leu Gly Ala Ile Val Lys Ala Ile Gly Xaa Val Val
1               5                   10                  15

His His Leu Gly Val Gly Leu
            20

(2) INFORMATION FOR SEQ ID NO:26:

(i) SEQUENCE CHARACTERISTICS:
        (A) LENGTH: 23 amino acids
        (B) TYPE: amino acid
        (C) STRANDEDNESS: single
        (D) TOPOLOGY: linear
```

(ii) MOLECULE TYPE: None (xi) SEQUENCE DESCRIPTION: SEQ ID NO:26:

Gly Phe His Phe Leu Gly Ser Val Ile His Ser Val Gly His Leu Ile
1               5                   10                  15

Lys His Val Gly Ile Ser Leu
            20

(2) INFORMATION FOR SEQ ID NO:27:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 9...0
            (D) OTHER INFORMATION: D-Ile (xi) SEQUENCE DESCRIPTION: SEQ ID NO:27:

Gly Tyr Lys Phe Leu Gly Gly Val Xaa His Gly Ile Gly His Leu Val
1               5                   10                  15

His Arg Val Ser Val Gly Ile
            20

(2) INFORMATION FOR SEQ ID NO:28:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 5...0
            (D) OTHER INFORMATION: D-Leu (xi) SEQUENCE DESCRIPTION: SEQ ID NO:28:

Ala Trp Arg Phe Xaa Gly Ala Ile Val Lys Gly Val Ala His Leu Leu
1               5                   10                  15

His Lys Ile Gly Val Ser Ile
            20

(2) INFORMATION FOR SEQ ID NO:29:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:29:

Phe Leu His Phe Ile Gly Ser Val Ile His Gly Ile Gly Arg Leu Val
1               5                   10                  15

Lys Lys Ile Gly Val Ala Leu
            20

(2) INFORMATION FOR SEQ ID NO:30:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 3...0
        (D) OTHER INFORMATION: D-Gln (xi) SEQUENCE DESCRIPTION: SEQ ID NO:30:

Tyr Val Xaa Phe Ile Gly Gly Val Leu Lys Ala Val Gly Lys Leu Val
1               5                  10                  15

His Arg Ile Gly Ile Ser Val
            20

(2) INFORMATION FOR SEQ ID NO:31:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

Trp Ile Gln Phe Leu Gly Ala Ile Ile His Ser Ile Gly His Ile Val
1               5                  10                  15

Arg His Val Gly Leu Ala Val
            20

(2) INFORMATION FOR SEQ ID NO:32:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

Gly Phe Lys Phe Leu Gly Ser Val Ile His Gly Ile Ala Arg Val Leu
1               5                  10                  15

His His Ile Gly Val Ala Val
            20

(2) INFORMATION FOR SEQ ID NO:33:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:33:

Phe Leu Xaa Xaa Ile Gly Xaa Xaa Ile His Xaa Xaa Gly Xaa Xaa Val
1               5                  10                  15

Xaa Xaa Xaa Xaa Xaa Xaa Xaa
            20

(2) INFORMATION FOR SEQ ID NO:34:

(i) SEQUENCE CHARACTERISTICS:

(A) LENGTH: 23 amino acids
(B) TYPE: amino acid
(C) STRANDEDNESS: single
(D) TOPOLOGY: linear (xi) SEQUENCE DESCRIPTION: SEQ ID NO:34:

Gly Ile Gly Lys Phe Leu His Ser Ala Gly Lys Phe Gly Lys Ala Phe
1               5                   10                  15

Val Gly Glu Ile Met Lys Ser
            20

(2) INFORMATION FOR SEQ ID NO:35:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:35:

Gly Ile Gly Lys Phe Leu His Ser Ala Gly Lys Phe Gly Lys Ala Phe
1               5                   10                  15

Val Asn Glu Ile Met Lys Ser
            20

(2) INFORMATION FOR SEQ ID NO:36:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:36:

Val Phe Gln Phe Leu Gly Lys Ile Ile His His Val Gly Asn Phe Val
1               5                   10                  15

His Gly Phe Ser His Val Phe
            20

(2) INFORMATION FOR SEQ ID NO:37:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:37:

Val Phe Gln Phe Leu Gly Arg Ile Ile His His Val Gly Asn Phe Val
1               5                   10                  15

His Gly Phe Ser His Val Phe
            20

(2) INFORMATION FOR SEQ ID NO:38:

(i) SEQUENCE CHARACTERISTICS:
        (A) LENGTH: 23 amino acids
        (B) TYPE: amino acid
        (C) STRANDEDNESS: single
        (D) TOPOLOGY: linear (ix) FEATURE:
        (A) NAME/KEY: Modified Base
        (B) LOCATION: 17...0
        (D) OTHER INFORMATION: o-methyl tyrosine (xi) SEQUENCE DESCRIPTION: SEQ ID NO:38:

```
Val Phe His Leu Leu Gly Lys Ile Ile His His Val Gly Asn Phe Val
1               5                   10                  15

Tyr Gly Phe Ser His Val Phe
            20
```

(2) INFORMATION FOR SEQ ID NO:39:

(i) SEQUENCE CHARACTERISTICS:
        (A) LENGTH: 23 amino acids
        (B) TYPE: amino acid
        (C) STRANDEDNESS: single
        (D) TOPOLOGY: linear (ix) FEATURE:
        (A) NAME/KEY: Modified Base
        (B) LOCATION: 17...0
        (D) OTHER INFORMATION: o-methyl tyrosine (xi) SEQUENCE DESCRIPTION: SEQ ID NO:39:

```
Ala Phe Lys Leu Leu Gly Arg Ile Ile His His Val Gly Asn Phe Val
1               5                   10                  15

Tyr Gly Phe Ser His Val Phe
            20
```

(2) INFORMATION FOR SEQ ID NO:40:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:40:

```
Leu Phe Lys Leu Leu Gly Lys Ile Ile His His Val Gly Asn Phe Val
1               5                   10                  15

His Gly Phe Ser His Val Phe
            20
```

(2) INFORMATION FOR SEQ ID NO:41:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO:41:

```
Phe Leu Arg Phe Ile Gly Ser Val Ile His Gly Ile Gly His Leu Val
1               5                   10                  15

His His Ile Gly Val Ala Leu
            20
```

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: Modified Base
        (B) LOCATION: 19...0
        (D) OTHER INFORMATION: Inosine
        (A) NAME/KEY: Modified Base
        (B) LOCATION: 22...0
        (D) OTHER INFORMATION: Inosine (xi) SEQUENCE DESCRIPTION: SEQ ID NO:42:

```
GTCGACTAGT CAYCAYGTNG GNAAYTTYGT                                    30
```

(2) INFORMATION FOR SEQ ID NO:43:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:43:

```
Leu Glu Glu Arg Lys Ser Glu Glu Glu Lys
 1               5                   10
```